(12) United States Patent
Thayumanavan

(10) Patent No.: US 8,420,121 B2
(45) Date of Patent: Apr. 16, 2013

(54) DRUG DELIVERY VEHICLES, METHODS OF MANUFACTURE, AND METHODS OF USE THEREOF

(75) Inventor: Sankaran Thayumanavan, Amherst, MA (US)

(73) Assignee: University of Massachusetts, Boston, MA (US)

( * ) Notice: Subject to any disclaimer, the term of this patent is extended or adjusted under 35 U.S.C. 154(b) by 99 days.

(21) Appl. No.: 12/845,126

(22) Filed: Jul. 28, 2010

(65) Prior Publication Data

US 2011/0200675 A1    Aug. 18, 2011

Related U.S. Application Data

(60) Provisional application No. 61/229,287, filed on Jul. 29, 2009.

(51) Int. Cl.
*A61K 9/14* (2006.01)
*A61K 31/44* (2006.01)

(52) U.S. Cl.
USPC ............ 424/487; 424/486; 424/484; 514/282

(58) Field of Classification Search .................. 424/487, 424/486, 484; 514/282
See application file for complete search history.

(56) References Cited

PUBLICATIONS

Georgiou et al., Biomacromolecules, 2008, 9, 574-582.*
Demosthenous et al., Macromolecules, 2002, 35, 2252-2260.*
Katz, Curr. Rheumatol Rep., 2008, 10(1), 11-18.*
Georgiades et al., Macromolecules, 2002, 35, 4903-4911.*
Kim et al., Smart Mater. Struct., 2004, 13, 317-322.*
Bulmus et al., Macromol. Biosci., 2007, 7, 446-455.*
Herber, et al.; "Exploitation of a pH-Sensitive Hydrogel Disk for CO2 Detection"; Sensors and Actuators B; 103; pp. 284-289; (2004).
Presentation; "Feedback Regulated Drug Delivery Systems (FRDDS) Based on Polymer Hydrogels & Vesicles"; presented by S. Thayumanavan, University of Massachusetts—Amherst; Mar. 3, 2009; 15 pages.

* cited by examiner

*Primary Examiner* — Abigail Fisher
(74) *Attorney, Agent, or Firm* — Cantor Colburn LLP

(57) ABSTRACT

Drug delivery vehicles that release one or more drugs, e.g., an opioid antagonist and/or an opioid, in response to changes in the chemistry of body fluids, specifically in response to changes in the partial pressure of $CO_2$ in the environment of the hydrogel are described. The drug delivery vehicles include hydrogels that swell or shrink in response to changes in the partial pressure of $CO_2$ in their environment, thus regulating release of an entrapped drug.

12 Claims, 16 Drawing Sheets

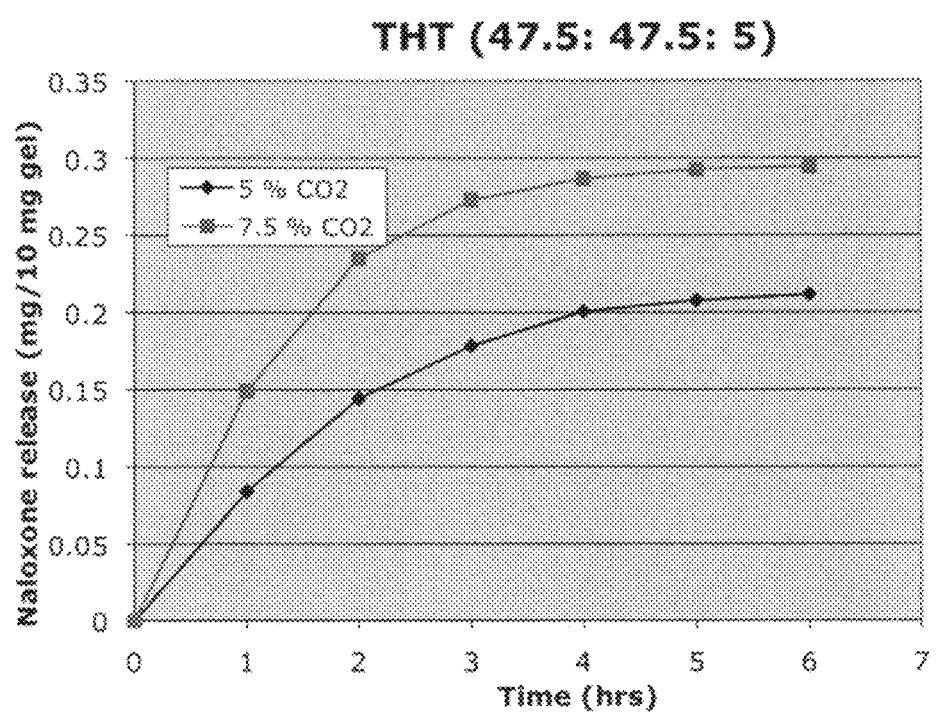

DRUG DELIVERY VEHICLES, METHODS OF MANUFACTURE, AND METHODS OF USE THEREOF

CROSS-REFERENCE TO RELATED APPLICATION

This application claims the benefit of U.S. Provisional Application No. 61/229,287, filed Jul. 29, 2009, which is incorporated by reference herein.

STATEMENT REGARDING FEDERALLY SPONSORED RESEARCH & DEVELOPMENT

The U.S. Government has certain rights in this invention pursuant to Grant No. W911NF-07-1-0462 awarded by DARPA through the Army Research Office.

BACKGROUND

This disclosure relates to formulations and methods for the controlled release of drugs, in particular the controlled release of opioids and opioid antagonists using hydrogels.

Hydrogels are materials that absorb solvents (in particular water), undergo rapid swelling without discernible dissolution, and maintain three-dimensional networks capable of reversible deformation. Hydrogels can be physically or chemically crosslinked. A number of aqueous hydrogels have been used in biomedical applications, such as soft contact lenses, wound management, and drug delivery. Hydrogels are advantageous for drug delivery as the composition of the hydrogel can often be adjusted to provide the desired release of an active agent.

Opioids are a class of analgesics used for pain management. One of the major limitations of opioid analgesics is their low therapeutic index: the toxic dose of a drug for 50% of the population ($TD_{50}$) divided by the minimum effective dose for 50% of the population ($ED_{50}$). There is little margin of error between an efficacious dose and a toxic dose (overdose) of an opioid. Compounding this problem is the extreme toxicity of opioids when dosage levels are too high. Opioid-induced toxicity leads to hypoventilation (respiratory depression), resulting in an increased concentration of $CO_2$ and a decreased concentration of $O_2$ in blood plasma. In extreme cases, when administered an overdose of an opioid, an individual can cease breathing entirely. Opioid antagonists, such as naloxone, naltrexone, nalmefene, and nalorphine, can be used to block the effects of opioids, reversing respiratory depression and other symptoms of opioid overdose. While opioid antagonists are effective, it is important to know when such administration is required, and preferably, before the individual is suffering from the physiological effects of an overdose.

In addition to use in clinical settings, opioid analgesics are commonly used in battlefield applications to ameliorate pain due to traumatic injuries. In battlefield settings, the stresses of battle can result in under or over dosing of patients, and overdosing can result in death. An opioid dosage form with controlled release features that are based on the individual's levels of opioid would be very advantageous in such systems.

There thus remains a need for compositions and methods for administering opioids and their antagonists that can be used to reduce the incidence of opioid toxicity.

SUMMARY

In one embodiment, a drug delivery vehicle comprises a first hydrogel comprising an opioid antagonist, wherein release of the opioid antagonist from the first hydrogel is stimulated by an increase in the concentration of $CO_2$ in the environment of the drug delivery vehicle; and a second hydrogel comprising an opioid, wherein release of the opioid from the second hydrogel is substantially $CO_2$-independent, or is decreased by an increase in the concentration of $CO_2$ in the environment of the drug delivery vehicle. In one embodiment, the hydrogel comprises a $CO_2$-sensitive group.

In another embodiment, a drug delivery vehicle comprises an opioid and a hydrogel stimulated by an increase in the partial pressure of $CO_2$, wherein the hydrogel comprises the reaction product of a composition comprising:

25 to 50% of an aminoallyl (meth)acrylate or salt thereof of Formula 9

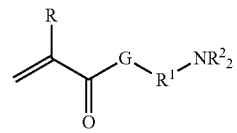

(9)

wherein G is oxygen or NR' where R' is hydrogen or $C_{1-3}$ alkyl group, R is hydrogen or methyl, $R^1$ is a straight chain or branched $C_{1-4}$ alkyl group, and each $R^2$ is independently hydrogen, or a labile group removable after polymerization conditions, 20 to 80 mol % of an acetal (meth)acrylate of Formula 5

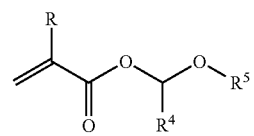

(5)

wherein R is hydrogen or methyl, and each $R^4$ and $R^5$ is independently a straight chain or branched $C_{1-4}$ alkyl group, or $R^4$ and $R^5$ together form a cycloaliphatic ring having a total of 5 to 7 carbon atoms.

1 to 25 mol % of a crosslinker of Formulas 6 a, b (6)

(a)

(6)

(b)

wherein each R is independently hydrogen or methyl, n is 1 to 4, and each $R^6$ and $R^7$ is independently hydrogen or a straight or branched chain $C_{1-3}$ alkyl group, or $R^6$ and $R^7$ together form a cycloaliphatic ring having a total of 5 to 6 carbon atoms or a cycloheteroaliphatic ring having 4 to 6 carbon atoms and an oxygen or sulfur ring atom, or a combination thereof.

Also disclosed are pharmaceutical compositions comprising the drug delivery vehicles disclosed herein and a pharmaceutically acceptable excipient.

In another embodiment, a method of regulating release of an opioid and/or opioid antagonist from a drug delivery vehicle comprises contacting the drug delivery vehicle with an increase in partial pressure of $CO_2$, wherein the drug delivery vehicle comprises the opioid antagonist in a first hydrogel that releases the opioid antagonist in response to the increase in partial pressure of $CO_2$, and/or wherein the drug delivery vehicle comprises the opioid in a second hydrogel that ceases release of the opioid in response to the increase in partial pressure of $CO_2$.

BRIEF DESCRIPTION OF THE DRAWINGS

FIG. 2 illustrates a mechanism of pH-based degradation of a hydrogel to release opioid antagonist.

FIG. 25 shows naloxone release from THPMA-co-HEMA-co-TMPTMA gels.

DETAILED DESCRIPTION

Disclosed herein are feedback-regulated drug delivery vehicles that control release one or more of an opioid antagonist and/or an opioid in response to a change in their environment (e.g., a change in the chemistry of surrounding body fluids), specifically in response to a change in the partial pressure of $CO_2$. It has been unexpectedly discovered that certain hydrogels shrink or swell in response to changes in the partial pressure of $CO_2$ in the surrounding environment of the hydrogel, thus providing a novel mechanism of regulating drug delivery. Importantly, the delivery vehicle response to $CO_2$ is reversible, that is, the release can be substantially turned on and off, which allows for cycling between different levels of $CO_2$.

In one embodiment, the drug delivery vehicle comprises an opioid antagonist in a hydrogel, wherein the release of opioid antagonist is $CO_2$-responsive. In this embodiment, the hydrogel releases the opioid antagonist in response to an increase in partial pressure of $CO_2$ in the environment of the hydrogel.

In another embodiment, the drug delivery vehicle comprises an opioid and a hydrogel, wherein the release of the opioid is $CO_2$-responsive. In this case, the $CO_2$-responsive release of the opioid means that the hydrogel ceases or decreases release of the opioid in response to an increase in partial pressure of $CO_2$ in the environment of the hydrogel.

In still another embodiment, the drug delivery vehicle comprises the opioid antagonist in a first hydrogel, wherein the release of opioid antagonist is $CO_2$-responsive, and an opioid in a second hydrogel, wherein the release of the opioid is either $CO_2$-independent or $CO_2$-responsive. The first hydrogel releases the opioid antagonist in response to an increase in partial pressure of $CO_2$, and when the release of opioid is $CO_2$-responsive, the second hydrogel substantially ceases or decreases release of the opioid in response to an increase in partial pressure of $CO_2$.

These drug delivery systems would be of great benefit in the case of traumatic injuries, particularly in battlefield settings. The systems release an antidote to opioid overdose (e.g., an opioid antagonist such as naloxone, naltrexone, nalmefene, or nalorphine) in response to elevated levels of $CO_2$ in blood plasma. Thus, patients receiving an accidental opioid overdose would automatically have an opioid overdose antidote released into the bloodstream so that the dangerous effects of the overdose would be reversed without further human intervention. Alternatively, the drug delivery system could decrease or shut off release of the opioid (e.g., morphine, fentanyl, alfentanil) in response to elevated levels of $CO_2$ in blood plasma, thus preventing further overdosing. In yet another embodiment, a drug delivery system could release the antidote as well as shut down release of the opioid in response to elevated levels of $CO_2$ in blood plasma.

Figure 1:
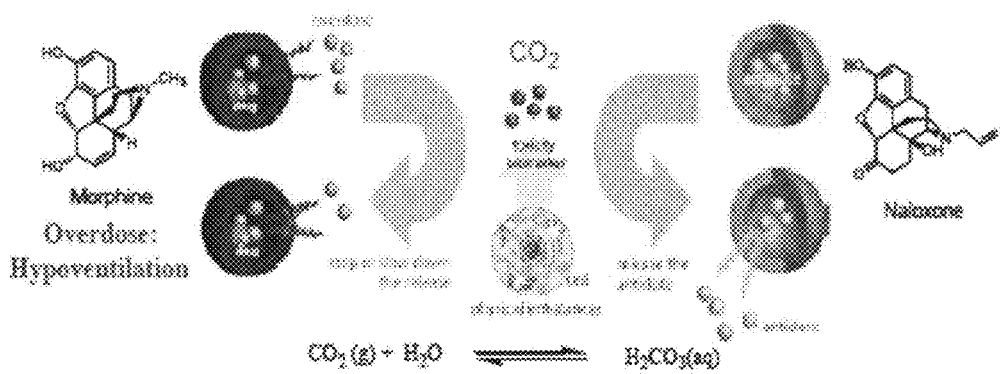
FIG. 1 shows a schematic representation of a drug delivery vehicle with controlled release of morphine at low $CO_2$ and reduced release of morphine and release of naloxone at high $CO_2$.

In particular, as illustrated schematically in FIG. 1, an increase in the partial pressure of $CO_2$ (e.g., under a condition of opioid overdose, or hypoventilation) results in an increase in the release of the opioid antagonist from the first hydrogel. Where the second hydrogel is $CO_2$-independent, the release of opioid is not affected. Where the second hydrogel is $CO_2$-responsive, the release of opioid is decreased or halted. Conversely, when the partial pressure of $CO_2$ is decreased (e.g., when normal ventilation is restored), the rate of release of the opioid antagonist from the first hydrogel is restored to its baseline level. Again, where the second hydrogel is $CO_2$- independent, the release of opioid is not affected. Where the second hydrogel is $CO_2$-responsive, the release of opioid is restored to its baseline level.

In these systems, a novel mechanism of feedback regulated automatic molecular release (FRAMR) is employed, in which the biomarker $CO_2$ is used as a trigger to either release an antidote in response to opioid overdose, to cease release of the opioid from the delivery vehicle, or both. Depending on the chemistry of the hydrogel, the hydrogel will shrink or expand in response to changes in $CO_2$ concentration in the fluid in which the hydrogel is located (such as blood), thus regulating the release of opioid antagonist or opioid. As used herein, a "$CO_2$-responsive hydrogel" is one that responds to a change in the concentration of $CO_2$ in a fluid containing the hydrogel.

As is known, a change in the concentration of $CO_2$ in a gaseous phase in contact with a fluid (such as blood) will result in a concomitant change in the concentration of $CO_2$ in the fluid. $CO_2$-responsive hydrogels therefore include those hydrogels that shrink or expand in response to a change in the concentration of $CO_2$ in a gaseous phase in contact with the fluid, for example a change from about 5.0 volume % to about 7.5 volume %, or about 7.5 volume % to about 5 volume % as indicated in Table 1.

TABLE 1

% $CO_2$ and partial pressure $CO_2$

| Volume % $CO_2$ | Partial pressure $CO_2$ (mmHg) | Opioid release |
|---|---|---|
| 4.0 | 29 | |
| 4.5 | 32 | |
| 5.0 | 36 | Release of opioid |
| 5.5 | 39 | |
| 6.0 | 43 | |
| 6.5 | 46 | |
| 7.0 | 50 | |
| 7.5 | 54 | Release of opioid antidote Optionally stop release of opioid |
| 8.0 | 57 | |
| 8.5 | 61 | |
| 9.0 | 64 | |

In a first embodiment, a drug delivery vehicle comprises a crosslinked hydrogel comprising $CO_2$-labile groups, and having dispersed therein an opioid antagonist, wherein the hydrogel swells in response to an increase in the concentration of $CO_2$ in the fluid environment of the hydrogel, and releases the opioid antagonist. By "releases the opioid antagonist," it means that release rate of the opioid antagonist increases from less than about 10 wt % release to greater than about 50 wt % release in response to a $CO_2$ partial pressure increase from about 36 to about 54 mmHg in the environment of the hydrogel.

Figure 2:
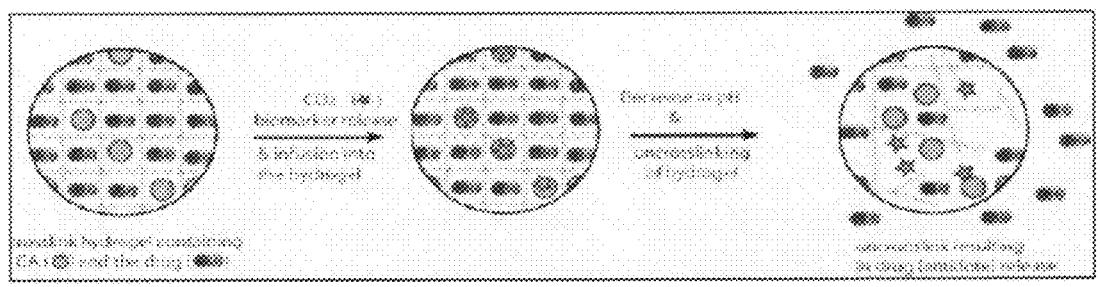
FIG. 2 shows the % $CO_2$ and partial pressure of $CO_2$ wherein opioid is released and opioid antagonist is released in an optimized treatment form as disclosed herein.

The release rate of the opioid antagonist from the hydrogel depends on the concentration of $CO_2$ in the fluid environment of the hydrogel, which in turn can depend on the concentration of $CO_2$ in the atmosphere in contact with the fluid environment. For example, in one aspect, at an atmospheric concentration of 5% $CO_2$, substantially no opioid antagonist released, but at an atmospheric concentration of 7.5% $CO_2$, the release rate is substantial. Without being held to theory, it is believed that an increased concentration of $CO_2$ in the atmosphere in contact with a medium containing the hydrogel results in a decrease in the pH of the gel environment. This could be due to the conversion of the increased amount of $CO_2$ in the medium to $H_2CO_3$, which is in equilibrium with $HCO_3^-$ and $H^+$. The pH change triggers the swelling of the hydrogel (due to hydrolysis of pH-sensitive groups in the hydrogel), which increases the release rate of the opioid antagonist. This effect is illustrated in FIG. 2, where the $CO_2$-labile group is a crosslinker. Further, as is understood by those skilled in the art, dissolution of $CO_2$ in a medium is a complex phenomenon that can result in the formation of a variety different species (e.g., $H_2CO_3$, $H^+$, $HCO_3^-$, the corresponding salts of $HCO_3^-$, and others) in equilibrium. Therefore, it is to be understood that reference herein to an increased or decreased amount of $CO_2$ in the medium in which the hydrogel is disposed is for convenience only, and encompasses the various species and equilibria that arise from an increase or decrease in the amount of dissolved $CO_2$ in the medium.

Hydrogels that release an opioid antagonist in response to an increase in the concentration of $CO_2$ in a fluid environment in which the hydrogel is disposed, and in particular which swell in response to an increase from about 5.0% to about 7.5% of $CO_2$ in a gaseous phase contacting the fluid environment, have acid labile groups. The acid labile groups are selected so as to affect the release of the opiate antagonist in response to an increase in the concentration of $CO_2$ in the medium, and can be, for example, acetal groups or ketal groups. Such hydrogels are formed from one or more polymerizable monomers, and one or more optional crosslinkers, wherein the acid labile groups are present in the monomer, the crosslinker, or both.

Polymerizable monomers and crosslinkers for the formation of hydrogels are widely known. Such compounds have polymerizable groups, for example, ethylenically unsaturated groups such as vinyl groups, acrylate or methacrylate groups (referred to herein for convenience as "(meth)acrylate" groups), or acrylamide or methacrylamide groups (referred to herein for convenience as "(meth)acrylamide" groups). Specific monomers for the formation of hydrogels include, for example, vinyl alcohol and water-soluble (meth)acrylates and (meth)acrylamides such 2-hydroxyethyl (meth)acrylate (HEMA), 1-hydroxyethyl (meth)acrylate, 3-hydroxypropyl (meth)acrylate, (meth)acrylic acid, (meth)acrylamide, and the like. Monomers with hydrophobic groups are often included in order to adjust the properties of the hydrogel, for example to increase the mechanical strength of the hydrogel. Crosslinkers for the formation of hydrogels are also known, and include a wide variety of difunctional, trifunctional, or higher functionality compounds.

The inventors hereof have found, however, that specific combinations of monomers and crosslinkers provide hydrogels that are responsive to the dissolved levels of $CO_2$ in the medium in which the hydrogel is disposed, and in particular that swell in response to an increased level of $CO_2$ in the medium. In one embodiment, the hydrogel comprises units formed by the polymerization of 80 to 99 mol % of HEMA and 5 to 15 mol % of an acetal-containing crosslinker having at least two ethylenically unsaturated groups, in particular (meth)acrylamide groups. Exemplary crosslinkers of this type include bis(meth)acrylamide acetals of Formula 1

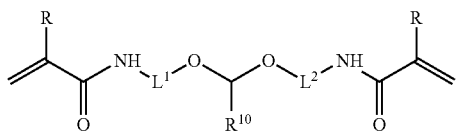

(1)

wherein each R is independently hydrogen or methyl.

Further in Formula 1, each $L^1$ and $L^2$ are independently a branched or unbranched $C_{1-4}$ alkylene or $C_{2-4}$ alkenylene, each of which can be unsubstituted or substituted with a hydroxy, carboxy, $C_{1-4}$ alkoxy, phenyl, or phenoxy group, wherein the phenyl or phenoxy group can be unsubstituted or substituted with 1 to 3 hydroxy, carboxy, $C_{1-4}$ alkoxy, phenyl, or phenoxy groups.

Still further in Formula 1, $R^{10}$ is a branched or unbranched $C_{1-10}$ alkylene, a $C_{2-10}$ alkenylene, or a phenyl group, each of which can be unsubstituted or substituted with a hydroxy, carboxy, $C_{1-4}$ alkoxy, phenyl, or phenoxy group.

In one embodiment, each R is independently hydrogen or methyl, each $L^1$ and $L^2$ are independently an unbranched $C_{2-4}$ alkylene which can be unsubstituted or substituted with a hydroxy, carboxy, $C_{1-4}$ alkoxy, phenyl, or phenoxy group, and $R^{10}$ is a phenyl group which can be unsubstituted or substituted with 1 to 3 $C_{1-4}$ alkoxy, phenyl, or phenoxy groups. Still more specifically, each R is independently hydrogen or methyl, each $L^1$ and $L^2$ are independently an unbranched $C_{2-3}$ alkylene, and $R^{10}$ is a phenyl group which can be unsubstituted or substituted with one to two $C_{1-4}$ alkoxy groups, specifically one $C_{1-4}$ alkoxy group. A specific monomer of Formula 1 is a bisacrylamide acetal of Formula 2

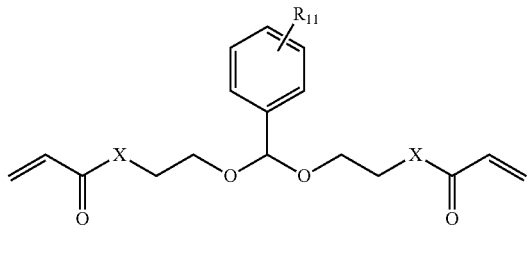

(2)

X = O, NH wherein $R^{11}$ is hydrogen, $C_{1-4}$ alkoxy, or —O—$(C_nH_{2n}O)_m$CH$_3$, where n=2-3 and m=0-9).

Scheme 1a shows an exemplary synthetic scheme for the preparation of a hydrogel formed from HEMA and the bisacrylamide acetal of Formula 2, and comprising the opioid antagonist naloxone sequestered therein. Scheme 1a further shows a theoretical mechanism for the release of the naloxone in response to an increased level of $CO_2$ in the medium in which the hydrogel is disposed. Without being bound by theory, it is believed that a decrease in the pH of the medium that results from the increased level of $CO_2$ results in hydrolysis of the $CO_2$-labile acetal groups in the bisacrylamide. The resultant swelling of the hydrogel increases the rate that the naloxone is released from the hydrogel.

Scheme 1a.

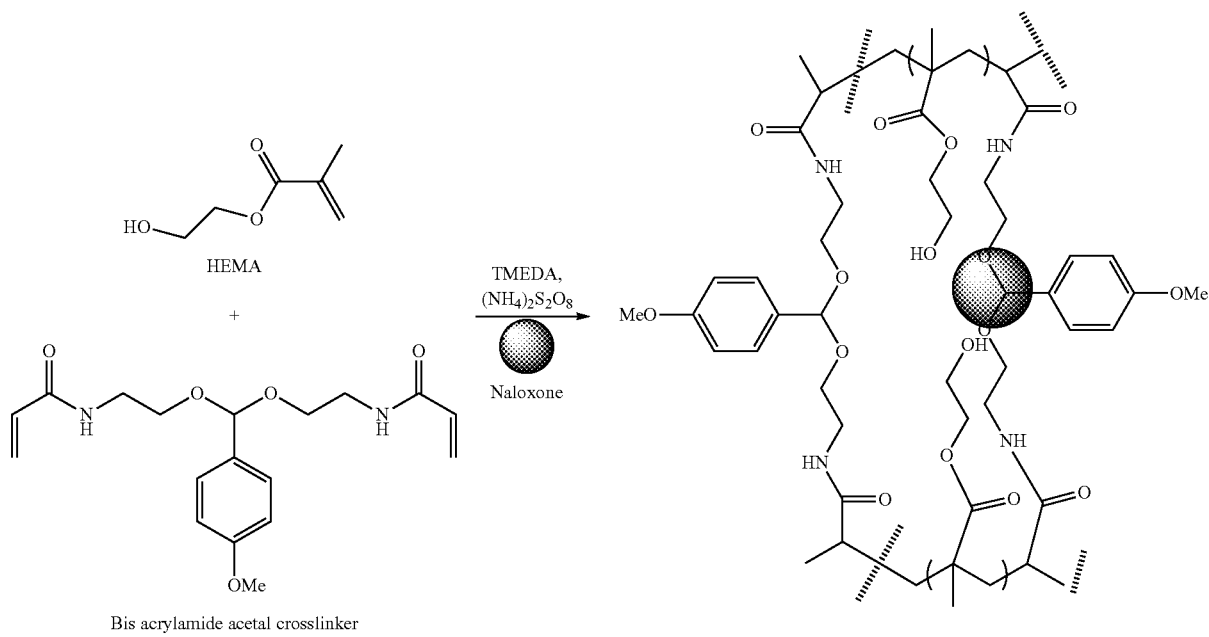

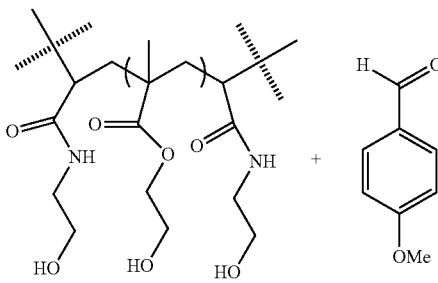
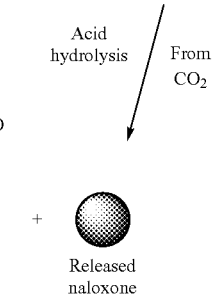

In another embodiment, the hydrogel comprises units formed by the polymerization of 80-99 mol % HEMA and 1 to 20 mol % of an acetal-containing crosslinker having two vinyl groups and two acetal functionalities, in particular a divinyl acetal of Formula 3

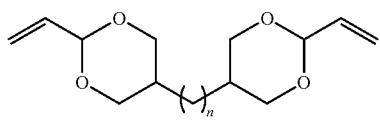
(3)

wherein n comprises 0 to 10 carbon atoms and is optionally substituted with a oxygen, nitrogen, or sulfur. In one embodiment, n is 0 to 3. In a specific embodiment, the divinyl acetal is of Formula 4

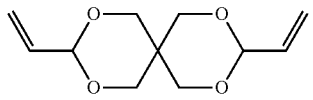
(4)

which is also referred to herein as DVSDO.

In still another embodiment, the hydrogel comprises units formed by the polymerization of 95 to 99 mol % of an acetal-containing (meth)acrylate monomer of Formula 5

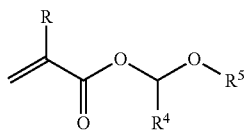
(5)

and 1 to 5 mol % of a di(meth)acrylate crosslinker of Formula 6

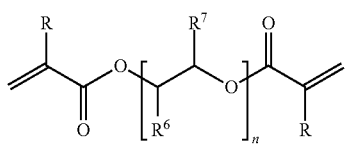
(6)

-continued

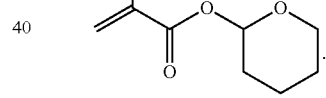

In the acetal (meth)acrylate of Formula 5, R is hydrogen or methyl, and each $R^4$ and $R^5$ is independently a straight chain or branched $C_{1-4}$ alkyl group, or $R^4$ and $R^5$ together form a cycloaliphatic ring having a total of 5 to 7 carbon atoms. In one embodiment, R is hydrogen or methyl, and each $R^4$ and $R^5$ is independently a straight chain or branched $C_{2-4}$ alkyl group, or $R^4$ and $R^5$ together form a cycloaliphatic ring having a total of 5 to 6 carbon atoms. A specific acetal (meth)acrylate of Formula 5 is 2-tetrahydropyranyl methacrylate (THPMA) of Formula 7

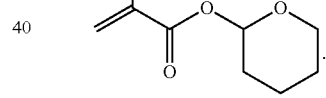
(7)

In the di(meth)acrylate crosslinker of Formula 6, each R is independently hydrogen or methyl, n is 1 to 4, and $R^6$ and $R^7$ is independently hydrogen or a straight or branched chain $C_{1-3}$ alkyl group or $R^6$ and $R^7$ together form a cycloaliphatic ring having a total of 5 to 6 carbon atoms or a cycloheteroaliphatic ring having 4 to 6 carbon atoms and an oxygen or sulfur ring atom, or a combination thereof. In a specific embodiment, each R is independently hydrogen or methyl, and $R^6$ and $R^7$ is independently hydrogen or a straight or branched chain $C_{1-3}$ alkyl group, or $R^6$ and $R^7$ together form a cycloaliphatic ring having a total of 5 to 6 carbon atoms. More specifically, R is hydrogen or methyl, and $R^6$ and $R^7$ are hydrogen, for example, the diacrylate of Formula 8

(8)

wherein n is 1 to 4.

In any one of the foregoing embodiments, the rate of release of the opioid antagonist from the hydrogels can be adjusted by adjusting the concentration of the $CO_2$-labile crosslinker or monomer in the hydrogel. Both the rate of release as well as the total amount released can be adjusted by adjusting the composition and amount of the hydrogel.

In one embodiment, a hydrogel suitable for $CO_2$-responsive release of an opioid antagonist comprises:

75 to 99 mol % of 2-hydroxyethyl methacrylate, specifically 85 to 95 mol %, and 1 to 25 mol % of the crosslinker of Formula (1), specifically 5-15 mol % of the crosslinker of Formula (2), wherein $R=CH_3$ or $CH_2CH_3$. A small amount of a different monomer or crosslinker or mixture thereof can optionally be present in order to adjust the properties of the hydrogel, provided that the presence of the monomers or crosslinkers does not substantially adversely affect the release properties of the hydrogel. For example, up to 25 mol %, specifically 10 mol % of a monomer other than HEMA, and up to 5 mol %, specifically 2 mol % of a different crosslinker may be employed.

In another embodiment, a hydrogel suitable for $CO_2$-responsive release of opioid antagonist comprises:

80 to 99 mol %, specifically 80 mol % of 2-hydroxyethyl methacrylate, and 1 to 20 mol %, specifically 20 mol % of a diacetal di(meth)acrylate crosslinker of Formula 3, specifically a diacetal diacrylate of Formula 4 as a crosslinker. A small amount of a different monomer or crosslinker or mixture thereof can optionally be present in order to adjust the properties of the hydrogel, provided that the presence of the monomers or crosslinkers does not substantially adversely affect the release properties of the hydrogel. For example, 25 mol %, specifically 10 mol % of a monomer other than HEMA, and up to 5 mol %, specifically 2 mol % of a different crosslinker may be employed.

In yet another embodiment, a hydrogel suitable for $CO_2$-responsive release of opioid antagonist comprises:

90 to 99 mol % of an acetal (meth)acrylate monomer of Formula 5, specifically the acetal methacrylate monomer of Formula 7, and 1 to 10 mol % of a di(meth)acrylate crosslinker of Formula 6, specifically the diacrylate of Formula 8 wherein n is 1 to 4. A small amount of a different monomer or crosslinker or mixture thereof can optionally be present in order to adjust the properties of the hydrogel, provided that the presence of the monomers or crosslinkers does not substantially adversely affect the release properties of the hydrogel. For example, 25 mol %, specifically 10 mol % of a monomer other than HEMA, and up to 5 mol %, specifically 2 mol % of a different crosslinker may be employed.

The hydrogel containing the opioid antagonist is used in combination with another drug delivery vehicle comprising another hydrogel and an opioid. The opioid release mechanism from this hydrogel can be $CO_2$-responsive or $CO_2$-independent.

In the $CO_2$-responsive, opioid-containing hydrogel, the hydrogel comprises amino groups. An increase in the concentration of $CO_2$ results in a decrease in the rate of opioid release from the hydrogel. Without being held to theory, it is believed that in these hydrogels, when $CO_2$ concentration in the medium in which the hydrogel is disposed is increased, the $CO_2$ will be converted to $HCO_3$ which will result in a fraction of the amino groups in the hydrogel being converted to carbamate groups. It is believed that an electrostatic interaction between the remaining amino groups and the carbamate groups will collapse the hydrogel structure, resulting in a decrease in the rate of release of opioid from the hydrogel.

As with the opioid antagonist hydrogels, the inventors hereof have found that only a certain combination of monomers and crosslinking agents provide hydrogels that are responsive to the dissolved levels of $CO_2$ in the medium in which the hydrogel is disposed, and in particular that contract in response to an increased level of $CO_2$ in the medium. Hydrogels that decrease the release rate of an opiate in response to an increase in the concentration of $CO_2$ in a fluid environment in which the hydrogel is disposed, and in particular which contract in response to an increase from about 5.0% to about 7.5% of $CO_2$ in a gaseous phase contacting the fluid environment, have amino groups. Such hydrogels are formed from one or more polymerizable monomers, and one or more optional crosslinkers, wherein the amino groups are present in the monomer, the crosslinker, or both. Further, the rate of release of the opioid antagonist from the hydrogels can be adjusted by adjusting the concentration of the amino groups in the hydrogel. Both the rate of release, as well as the total amount released can be adjusted by adjusting the composition of the hydrogel.

In one embodiment, a $CO_2$-responsive hydrogel for entrapment of opioids comprises units derived from the reaction of a composition comprising 25 to 50 mol %, specifically 30 to 45 mol % of an aminoalkyl (meth)acrylate of Formula 9

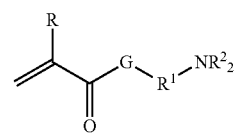

(9)

wherein G is oxygen or NR' where R' is hydrogen or $C_{1-3}$ alkyl group, R is hydrogen or methyl, $R^1$ is a straight chain or branched $C_{1-4}$ allylene group, and each $R^2$ is independently hydrogen, $C_{1-4}$ allyl, or a labile group removable under additional reaction conditions, e.g., an acyl group. Specifically, R is hydrogen or methyl, $R^1$ is a straight chain $C_{2-4}$ alkylene group, and each $R^2$ is methyl. The aminoalkyl (meth)acrylate can be the 2-(dimethylamino)ethyl (meth)acrylate of Formula 10

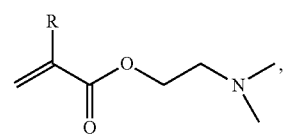

(10)

preferably wherein R is methyl. The corresponding acid salt of the aminoalkyl (meth)acrylates can be used, for example a halide (e.g., chloride), phosphate, sulfate or other salt.

The composition for the formation of this $CO_2$-responsive hydrogel further comprises 20 to 80 mol %, specifically 40 to 70 mol % of an acetal (meth)acrylate of Formula 5

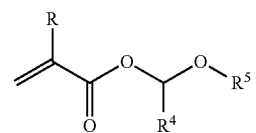

(5)

as described above, and 1 to 25 mol %, specifically 1-5 mol % of a crosslinker of Formula 6

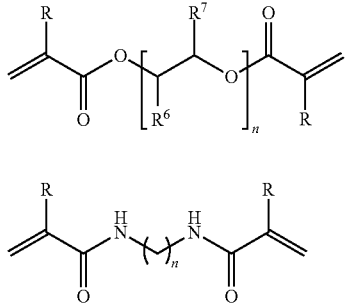

(6)

as described above. In a specific embodiment, the hydrogel is formed by polymerization of a composition comprising 25 to 50 mol % of 2-aminoethyl methacrylate, 40 to 70 mol % of 2-tetrahydropyranylmethacrylate, and 1 to 10 mol % of a diacrylate of Formula 8 wherein n is 1 to 4. In any of the foregoing embodiments, a small amount of a different monomer, a crosslinker, or a mixture thereof can optionally be present in order to adjust the properties of the hydrogel, provided that the presence of the monomers or crosslinkers does not substantially adversely affect the release properties of the hydrogel. For example, 25 mol %, specifically 10 mol % of a monomer other than HEMA, and up to 5 mol %, specifically 2 mol % of a different crosslinker may be employed.

In another embodiment, the drug delivery vehicle comprises an opioid and a hydrogel, wherein the release of the opioid is $CO_2$-independent. While it is possible to use a wider variety of hydrogels as the $CO_2$-independent hydrogel, it has been found that hydrogels based on (meth)acrylic acid, a salt of a (meth)acrylic acid, or an ester of (meth)acrylic acid, together with a crosslinker of Formula (6) are suitable for use with the $CO_2$-responsive hydrogel containing the opioid antagonist. The hydrogels can further comprise other monomers and/or crosslinkers for adjusting the characteristics of the hydrogels.

For example, a $CO_2$-independent hydrogel for the release of an opioid comprises units can be obtained by the polymerization of a composition comprising:

30 to 99 mol % of a (meth)acrylic acid or acid salt of Formula 11

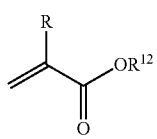

(11)

wherein R is hydrogen or methyl and $R^{12}$ is hydrogen, a counterion, for example ammonium or an alkali metal such as $Na^+$ or $K^+$;

0 to 70 mol % of a (meth)acrylate ester of Formula 12

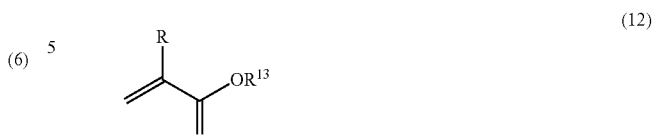

(12)

wherein R is hydrogen or methyl, $R^{13}$ is a branched or straight chain $C_{1-6}$ allyl group optionally substituted with a hydroxy, or $C_{1-3}$ alkoxy group, or a poly(alkleneglycol) ether group of Formula $-(CH_2)_mO[(C_mH_{2m}O)]_pR^{15}$, wherein m is 2-4, p is 1-8, and $R^{15}$ is hydrogen or a $C_{1-4}$ allyl group; and 1 to 10 mol % of a crosslinker of Formula 6

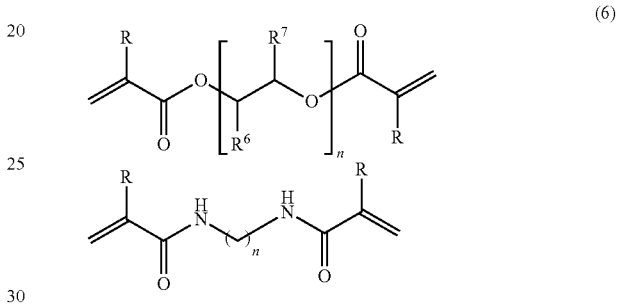

(6)

as described above, specifically a crosslinker of Formula 8 wherein n is 1-4.

More specifically, controlled release hydrogels can be obtained by polymerization of a composition comprising:

30 to 99 mol % of a (meth)acrylic acid, specifically acrylic acid;

0 to 70 mol % of a (meth)acrylic acid ester of Formula 12

(12)

wherein $R^{13}$ is methyl, tert-butyl, hydroxyethyl, or $-(C_2H_4O)_4CH_3$; and 1 to 10 mol %, specifically 1 to 5 mol % and more specifically 3 to 5 mol % of a di(meth)acrylate crosslinker of Formula 6 as described above, specifically a diacrylate crosslinker of Formula 8 wherein n=1 to 4.

The release of opioid can be sustained, burst, or controlled, depending on the identity and relative amounts of each of the monomers and crosslinkers used to form the hydrogel.

For example, in one embodiment, opioid release is sustained release and the hydrogel is formed from a composition comprising:

75-99 mol %, specifically 90 to 99 mol %, and more specifically 95 mol % of an (alkyl)acrylic acid, specifically acrylic acid or methacrylic acid, and 1 to 25 mol %, specifically 1 to 10 mol % and more specifically 5 mol % of a crosslinker of Formula 6 as described above, specifically of Formula 8 wherein n is 1 to 4.

In another embodiment, opioid release is burst release and the hydrogel is formed from a composition comprising:

75-99 mol %, specifically 90 to 99 mol %, and more specifically 95 mol % of a salt of an (alkyl)acrylic acid, specifically sodium acrylate; and 1 to 25 mol %, specifically 1 to 10 mol % and more specifically 5 mol % of a crosslinker of Formula 6, specifically of Formula 8 wherein n is 1 to 4.

In another embodiment, opioid release is burst release and the hydrogel is formed from a composition comprising:

75-99 mol %, specifically 90 to 99 mol %, and more specifically 95 mol % of a salt of a sodium salt of acrylic acid; and 1 to 25 mol %, specifically 1 to 10 mol % and more specifically 5 mol % of a crosslinker of Formula 6, specifically of Formula 8 wherein n is 1 to 4.

In one aspect, controlled release of opioid is achieved by physically mixing 1:99 to 99:1 hydrogel A to hydrogel B, wherein hydrogel A is an acrylic acid or methacrylic acid hydrogel and a hydrogel B is a sodium acrylate hydrogel as described above, in ratios of 1 to 99 mol % to 99 to 1 mol %.

$CO_2$-independent hydrogels can be obtained in another embodiment by polymerization of a composition comprising:

75 mol %, specifically 90 to 95 mol %, more specifically 95 or 98 mol % of a (meth)acrylic acid, specifically methacrylic acid;

1 to 25 mol %, specifically 1 to 10 mol % of a (alkyl)acrylic acid ester of Formula 12

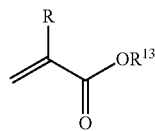

(12)

wherein R is hydrogen or methyl, specifically methyl, and $R^{13}$ is a branched or straight chain $C_{1-6}$ alkyl group optionally substituted with a hydroxy, or $C_{1-3}$ alkoxy group, or a poly (alkyleneglycol) ether group of Formula —$(CH_2)_mO$ $[(C_mH_{2m}O)]_pR^{15}$, wherein m is 2-4, p is 1-8, and $R^{15}$ is hydrogen or a $C_{1-4}$ alkyl group, specifically methyl, tert-butyl, hydroxyethyl, or —$(C_2H_4O)_4CH_3$; and 1 to 5 mol %, and more specifically 3-5 mol % of a di(meth)acrylate crosslinker of Formula 6 as described above, specifically a diacrylate crosslinker of Formula 8 wherein n is 1 to 4.

In another embodiment, controlled release of opioid is accomplished with a hydrophilic-modified acrylic acid formed from a composition comprising:

75 to 99 mol %, specifically 95 to 99 mol %, and more specifically 95-98 mol % of N-methacryloyl glutamic acid (MAGA);

1 to 25 mol %, specifically 1 to 5 mol %, and more specifically 2 to 5 mol % a crosslinker of Formula 6, specifically of Formula 8, wherein n=1 to 4, and more specifically tetra(ethylene glycol) diacrylate (TEGDA).

In another aspect of this disclosure, the hydrogels disclosed herein are prepared as nanoparticles (nanogels) that are suitable for parenteral administration (e.g., intravenous injection). A nanogel is a hydrogel in the form of nanoparticles, that is, particles having diameters of less than 500 nm.

In one embodiment, a pharmaceutical composition comprises the hydrogels as described herein, an opiate or opiate antagonist, and a pharmaceutically acceptable excipient. Administration of the pharmaceutical compositions is accomplished by an effective route, e.g., orally or parenterally. Methods of parenteral delivery include topical, intra-arterial, subcutaneous, intramedullary, intravenous, intranasal, intramuscular or intraosseous administration. In addition to the hydrogel and the drug, the pharmaceutical compositions can contain suitable pharmaceutically acceptable carriers comprising excipients and other compounds that facilitate administration of the biologically active molecules to a subject. Excipients include, for example, glidants, dissolution agents, surfactants, diluents, binders, disintegrants and/or lubricants.

Diluents include, for example, pharmaceutically acceptable inert fillers such as microcrystalline cellulose, lactose, sucrose, fructose, glucose dextrose, or other sugars, dibasic calcium phosphate, calcium sulfate, cellulose, ethylcellulose, cellulose derivatives, kaolin, mannitol, lactitol, maltitol, xylitol, sorbitol, or other sugar alcohols, dry starch, saccharides, dextrin, maltodextrin or other polysaccharides, inositol or mixtures thereof. Glidants are used to improve the flow and compressibility of ingredients during processing. Glidants include, for example, colloidal silicon dioxide, a sub-micron fumed silica that can be prepared by, for example, vapor-phase hydrolysis of a silicon compound such as silicon tetrachloride. Disintegrants include, for example, starches, sodium starch glycolate, crospovidone, croscarmellose, microcrystalline cellulose, low substituted hydroxypropyl cellulose, pectins, potassium methacrylate-divinylbenzene copolymer, poly(vinyl alcohol), thylamide, sodium bicarbonate, sodium carbonate, starch derivatives, dextrin, beta cyclodextrin, dextrin derivatives, magnesium oxide, clays, bentonite and mixtures thereof. Lubricants include agents that act on the flowability of the powder to be compressed include but are not limited to silicon dioxide such as Aerosil 200, talc; stearic acid, magnesium stearate, calcium stearate, hydrogenated vegetable oils, sodium benzoate, sodium chloride, leucine carbowax, magnesium lauryl sulfate, and glyceryl monostearate.

In one embodiment, if the pharmaceutical composition is designed for oral administration, the hydrogel can be in macrogel or microgel form. If, however, the pharmaceutical composition is for intravenous or intraosseous administration, the hydrogel can be in nanogel form so that needles and tubes, etc. are not clogged by the composition.

On one embodiment, the hydrogel further comprises an enzyme that is either covalently or noncovalently attached to the hydrogel. The enzyme can be present, for example, during synthesis of the hydrogel. In one embodiment, the enzyme is carbonic anhydrase. Carbonic anhydrase is an enzyme that is capable of catalyzing the reaction between $CO_2$ and water.

The invention is further illustrated by the following non-limiting examples. In general, release experiments were performed at least twice.

EXAMPLE 1

Poly(Acrylamide acetal-HEMA) Based Hydrogel for the Controlled and $CO_2$ Dependent Release of Naloxone Scheme 1b. Acid-degradable naloxone-loaded hydrogel.

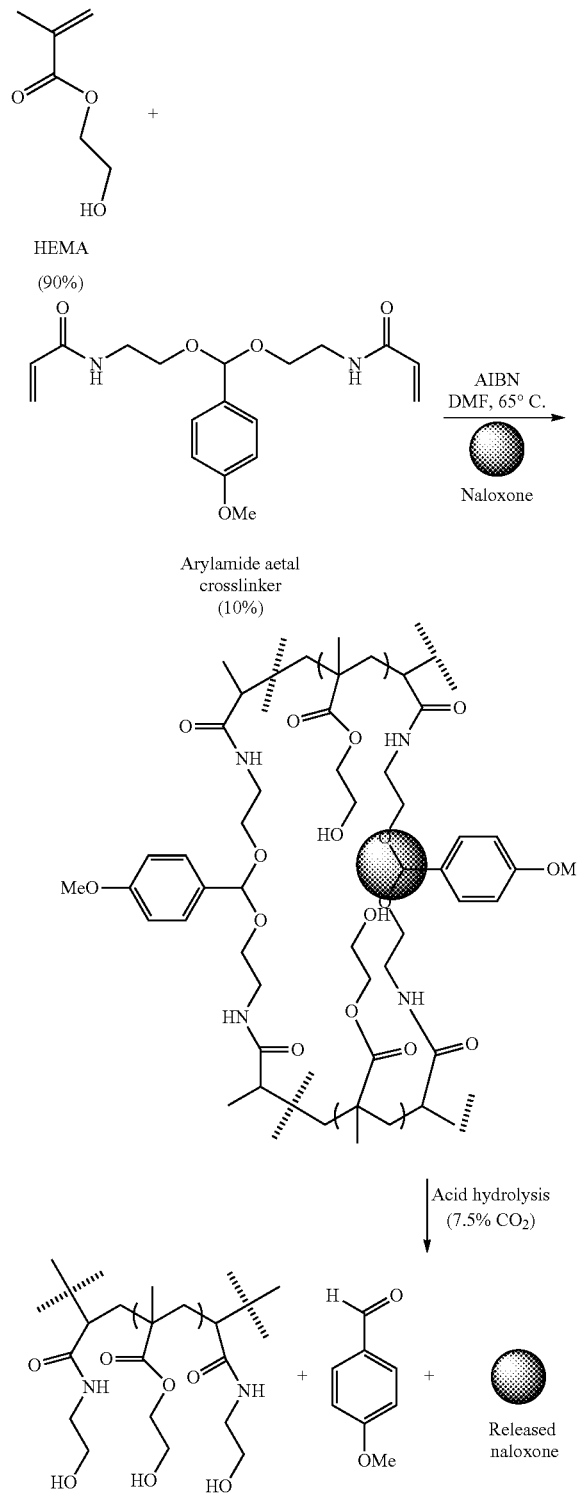

Materials: Materials were obtained from commercial suppliers. Tetrahydrofuran was distilled under a nitrogen atmosphere from Na/benzophenone immediately prior to use. P-Toluenesulfonic acid was recrystallized from toluene. N-(2-Hydroxyethyl)-2,2,2-trifluoroacetamide was freshly distilled before use. The chemical structures of the monomer and cross-linker are given in Scheme 1a and Scheme 1b.

The therapeutically active substance, naloxone, was from Sigma-Aldrich® Corp., St. Louis, Mo., USA, as the hydrochloride salt, and was used without further purification. Its structure is:

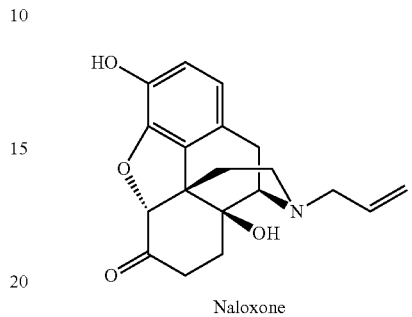

Naloxone

Bisacrylamide acetal crosslinker was synthesized according to the literature-reported method.

Synthesis of naloxone-loaded hydrogels: Two series of acetal-HEMA based hydrogels were synthesized by free-radical polymerization at various monomer and crosslinker ratios. The HEMA/Acetal crosslinker mole ratios used were 90/10 (Gel I) and 85/15 (Gel II). Briefly, the bisacrylamide acetal crosslinker, HEMA and naloxone (10 mg) were dissolved in 1 mL anhydrous DMF and the mixture was shaken thoroughly until the formation of homogeneous solution. The exact amounts of the monomer and crosslinker used for synthesis are shown in Table 2. The initiator AIBN (0.15 mole %) was added and the feed mixture was purged with argon for 15 minutes to remove dissolved oxygen, then the reaction vials were sealed and placed in a bath at 65° C. for 24 hours.

TABLE 2

Feed composition and % yields of polymerization and encapsulation.

| Hydrogel (sample code) Composition (%) | HEMA/mg | Acetal crosslinker/ mg | Polymerization yield (%) | Naloxone encapsulation efficiency (%) |
| --- | --- | --- | --- | --- |
| GEL I-10 | 315 | 100 | 90 | 85 |
| GEL II-15 | 200 | 100 | 86 | 75 |

Purification of hydrogels: The hydrogels were first washed with diethyl ether many times to remove the unreacted acetal crosslinker and then washed with PBS (pH 8) buffer to remove any impurities and unreacted species. Analysis of the washing solution demonstrated essentially quantitative gel entrapment of naloxone (Table 2). The resulting gels were dried at first in air for 2 days and then in a vacuum oven at 30° C. until no change in weight was observed.

Drug release measurement: The in vitro drug release was carried out at 37° C. to investigate the responsive nature of the hydrogel by measuring naloxone release profiles at 5 and 7.5% $CO_2$. First, 25 mg of Gel I and 15 mg of Gel II of naloxone-loaded hydrogels were placed in 1 mL of pH 7.4 PBS buffer (0.1 M) in two separate vials (2×25 mg and 2×15 mg). Then the vials were placed in a shaking water bath, maintained at 37° C. (shaking frequency of 70 rpm). Each vial was purged with two different percentages of $CO_2$ (one with 5% and the other with 7.5% of each composition). After purging CO₂ for one hour in shaking water bath, the solutions in each of the vials were removed as completely as possible, and the volumes, $V_1$ (mL), are measured. The release medium was changed entirely with fresh PBS solutions of an equal volume (1 mL of pH 7.4 PBS buffer) and the vials were again purged with $CO_2$. The amount of naloxone loaded in the studies was 1 mg. The concentrations of naloxone, $c_i$ (µg/mL), in the collected samples were analyzed by measuring the UV absorbance at 281 nm. At each time point, the total amount of drug released, $m_i$ (µg), was calculated by $m_i = c_i \cdot V_i + \Sigma m_{i-1}$. Finally, the percentage of total drug released at each time point was calculated by $m_i/\Sigma m_i \times 100\%$. The results are presented in terms of cumulative release as a function of time.

Figure 3:
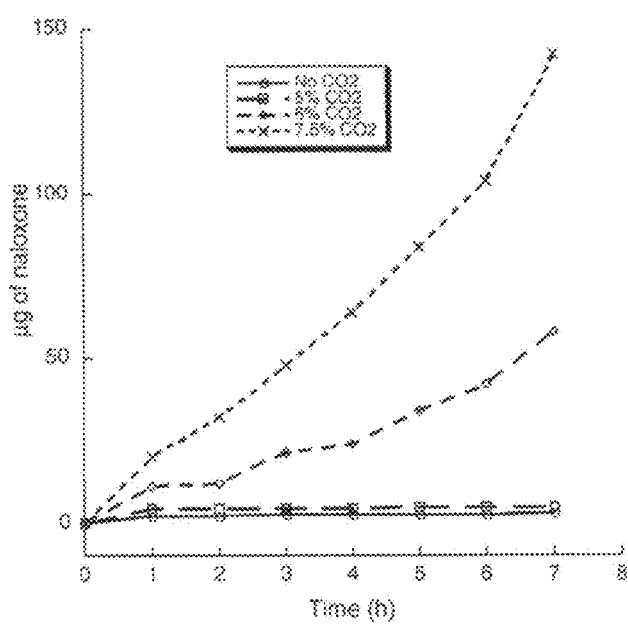
FIGS. 3 and 4 show the time and $CO_2$-responsive release of naloxone from an acrylamide acetal-HEMA hydrogel.
Figure 4:
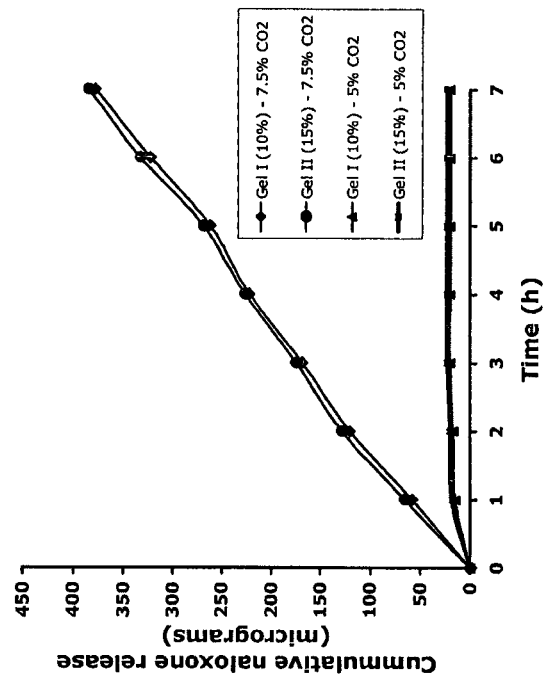

The release of naloxone from the naloxone-loaded hydrogel is shown as time- and % COT-responsive profiles in FIGS. 3 and 4. As predicted from the molecular design of the gel, the rate of naloxone release is % $CO_2$-responsive. At 7.5% $CO_2$, the acetal crosslinks hydrolyze rapidly and the encapsulated naloxone is released (FIG. 3). Approximately 36% of the naloxone is released and 12 hours are required for the hydrogel to completely release its contents. At 5% $CO_2$, release of the entrapped naloxone is significantly slower as only 9% of the encapsulated naloxone is released after 7 hours (FIG. 4). The observed naloxone release profile at 7.5% $CO_2$ is noteworthy because the $CO_2$ percentage during hyperventilation is in the range of 7.2-7.5%. As shown in FIG. 1b, in this range of $CO_2$ the hydrogel start to degrade effectively, thereby allowing the release of the loaded naloxone.

Figure 5:
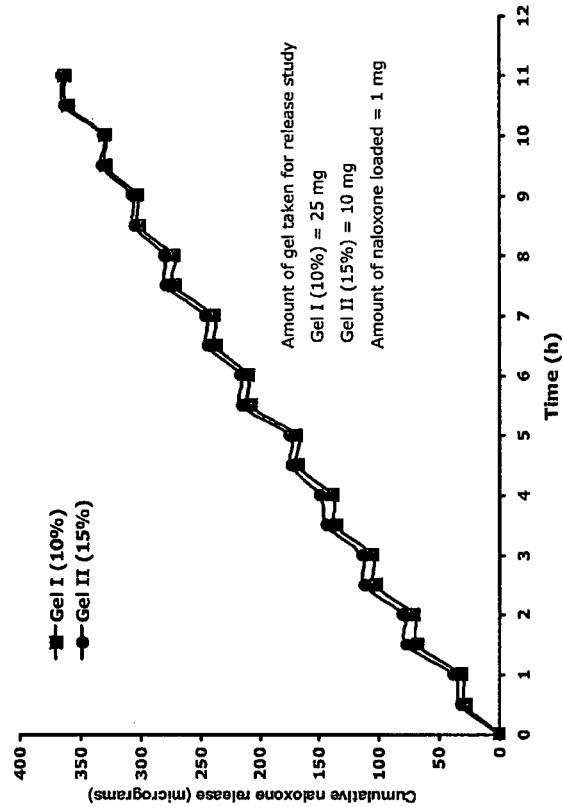
FIG. 5 shows the time and $CO_2$-responsive release of naloxone from an acrylamide acetal-HEMA hydrogel subjected to cycling between 5% and 7.5% $CO_2$.

Cycling study at 5% and 7.5% $CO_2$. The $CO_2$-responsive release profile was carried by cycling the $CO_2$ level between 5% and 7.5% $CO_2$. First, 25 mg of Gel I and 15 mg of Gel II were placed in 1 mL of pH 7.4 PBS buffer (0.1 M) in two separate vials (1×25 mg and 1×15 mg). Then the vials were placed in a shaking water bath, maintained at 37° C. (shaking frequency of 70 rpm). Each vial was purged with 7.5% $CO_2$ for first one hour. The solutions in each of the vials was removed as completely as possible for analysis and the release medium was changed entirely with fresh PBS solution of an equal volume. For the second one hour, the gels were purged with 5% $CO_2$. The cycling study was carried out so that the gels experienced 7.5% $CO_2$ for the first one hour and then 5% $CO_2$ for the second 1 hour. The results are presented in terms of cumulative release as a function of time (FIG. 5). All promising releasing experiments are performed twice.

Summary: The release of naloxone from acrylamide acetal-HEMA hydrogels in response to two different percentages of $CO_2$ (5 and 7.5%) was studied. At 5% $CO_2$, the cross-linker remains largely intact, and the release is significantly slower than at 7.5% $CO_2$, where hydrolysis of the acetal crosslinker results in more rapid release.

EXAMPLE 2

Poly(DVSDO-HEMA) Based Hydrogel for the Controlled and $CO_2$ Dependent Release of Naloxone

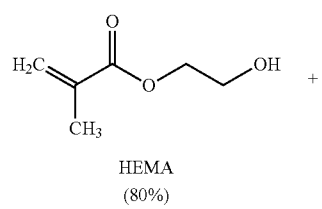

HEMA
(80%)

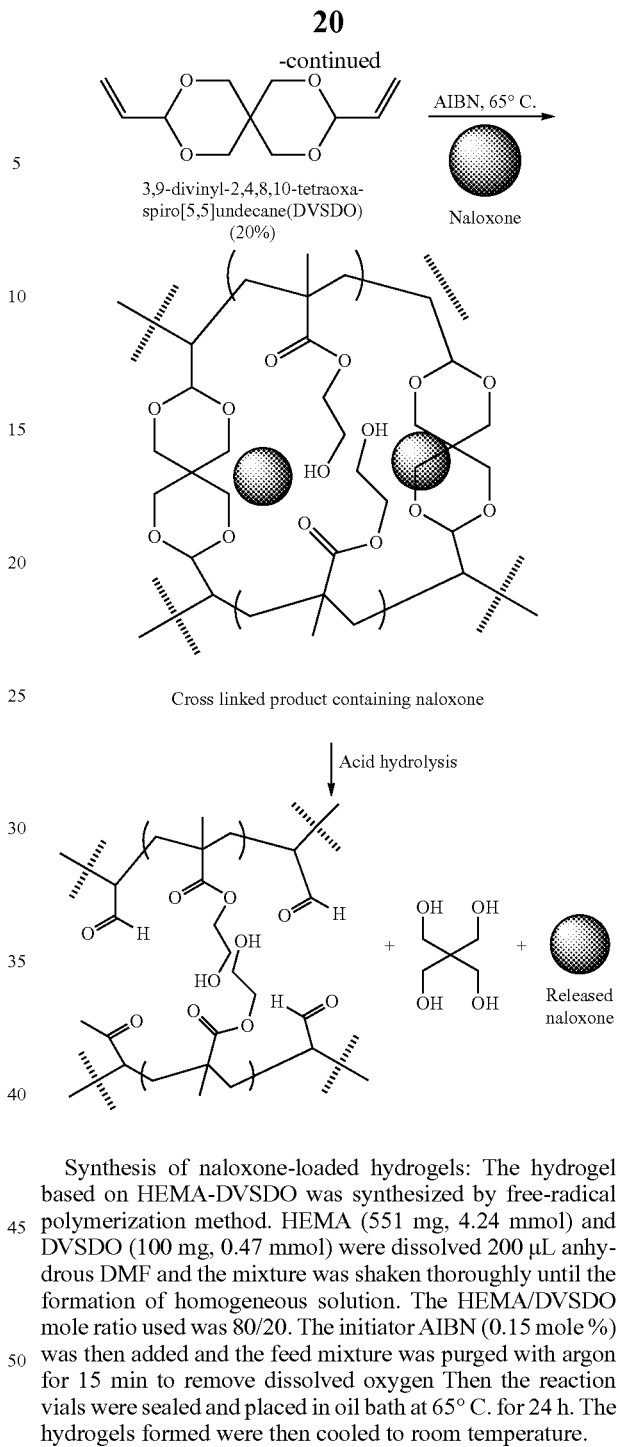

Synthesis of naloxone-loaded hydrogels: The hydrogel based on HEMA-DVSDO was synthesized by free-radical polymerization method. HEMA (551 mg, 4.24 mmol) and DVSDO (100 mg, 0.47 mmol) were dissolved 200 µL anhydrous DMF and the mixture was shaken thoroughly until the formation of homogeneous solution. The HEMA/DVSDO mole ratio used was 80/20. The initiator AIBN (0.15 mole %) was then added and the feed mixture was purged with argon for 15 min to remove dissolved oxygen Then the reaction vials were sealed and placed in oil bath at 65° C. for 24 h. The hydrogels formed were then cooled to room temperature.

TABLE

Feed composition and % yields of polymerization and encapsulation.

| Hydrogel (sample code) Composition (%) | HEMA/mg | DVDSO crosslinker/ mg | Polymerization yield (%) | Naloxone encapsulation efficiency (%) |
|---|---|---|---|---|
| HEMA/DVSDO (I-139) | 551 | 100 | 90 | 78 |

Purification of hydrogels: The hydrogels were first washed with diethyl ether many times to remove the unreacted crosslinker and then washed with PBS (pH 8) buffer to remove any impurities and unreacted species. Analysis of the washing solution demonstrated essentially quantitative gel entrapment of naloxone (Table). The resulting gels were dried at first in air and then in a vacuum oven at 30° C. until no change in weight was observed.

Figure 6:
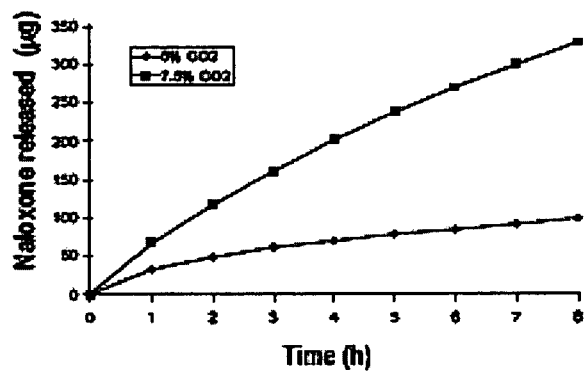
FIG. 6 show the time and $CO_2$-responsive release of naloxone from a DVSDO-HEMA hydrogel.

The release of naloxone from the naloxone-loaded hydrogel is shown as time- and % $CO_2$-responsive profiles in FIG. 6. As predicted from the molecular design of the gel, the rate of naloxone release is % $CO_2$-responsive. At 7.5% $CO_2$, the DVSDO crosslinks hydrolyze rapidly and the encapsulated naloxone is released (FIG. 6). Approximately 85% of the naloxone is released over 11 hours at 7.5% $CO_2$. At 5% $CO_2$, release of the entrapped naloxone is significantly slower, with only 26% released at 24 hours.

Summary: The release of naloxone from DVSDO-HEMA hydrogels in response to two different percentages of $CO_2$ (5 and 7.5%) was studied. At 5% $CO_2$, the release is comparatively slower than at 7.5% $CO_2$ where hydrolysis of the DVSDO crosslinker results in more rapid release.

EXAMPLE 3

Poly(THPMA-EGDA) Based Hydrogel for the Controlled- and $CO_2$-Dependent Release of Naloxone Scheme 2. Acid-degradable naloxone-loaded hydrogel.

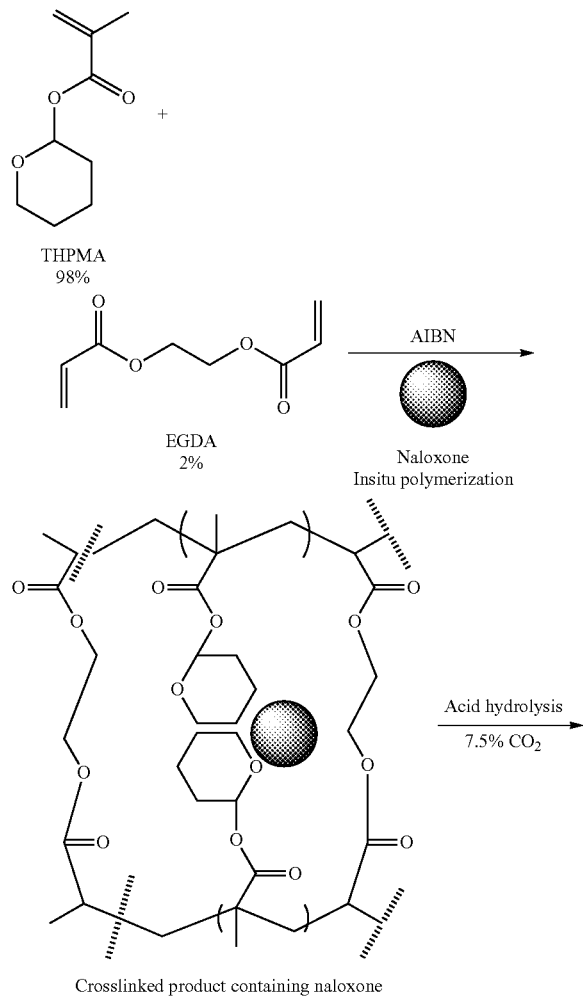

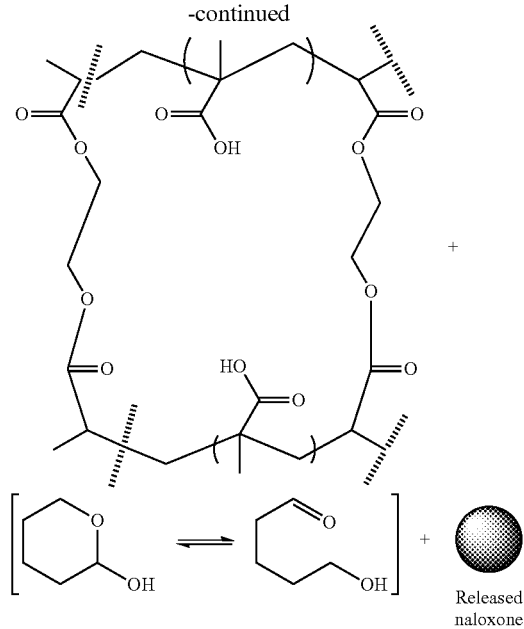

Materials: Methacrylic acid (MAA), 3,4-dihydro-2H-pyran (DHP) and ethylene glycoldiacrylate (EGDA) were purchased from Aldrich and used as reactants in the synthesis of the hydrogel. Azobisisobutyronitrile (AIBN) was purchased from Aldrich and recrystallized in methanol prior to use. The chemical structures of the monomers and crosslinker are shown in Scheme 2. All other reagents and organic solvents were used as chemical grade.

Synthesis of naloxone-loaded hydrogels: THPMA (2-tetrahydropyranylmethacrylate) was synthesized using a prior art method. The hydrogel based on THPMA-EGDA was synthesized by a free-radical polymerization method. THPMA (100 mg, 0.55 mmol) and EGDA (3.1 mg, 0.02 mmol) were dissolved 1 mL anhydrous DMF and the mixture was shaken thoroughly until the formation of homogeneous solution. The THPMA/EGDA mole ratio used was 98/2. The initiator AIBN (0.15 mole %) was then added and the feed mixture was purged with argon for 15 minutes to remove dissolved oxygen. Then the reaction vials were sealed and placed in a bath at 65° C. for 24 hours. The hydrogels formed were then cooled to room temperature.

Purification of hydrogels: The hydrogels were first washed with diethyl ether several times to remove the unreacted THPMA and then washed with PBS (pH 8) buffer to remove any impurities and unreacted species. Analysis of the washing solution demonstrated essentially quantitative gel entrapment of naloxone (Encapsulation efficiency=75%). The resulting gels were dried at first in air for 2 days and then in a vacuum oven at 30° C. until no change in weight was observed.

Drug release profile: The in vitro drug release was carried out at 5 and 7.5% $CO_2$ using the protocol of example 1 except the amount of gel taken for release study was 10 mg and the amount of naloxone loaded was 600 μg. The release of naloxone from the naloxone loaded hydrogel was evaluated as time- and % $CO_2$-responsive profiles in FIG. 7. As predicted from the molecular design of the gel, the rate of naloxone release is found to be % $CO_2$ dependent. At 7.5% $CO_2$, the $CO_2$-labile bond in THPMA is cleaved and the encapsulated naloxone is released (see FIG. 7). Approximately 0.83 mg/min of the naloxone is released and 12 hours is required for the hydrogel to completely release its contents. At 5%

Figure 7:
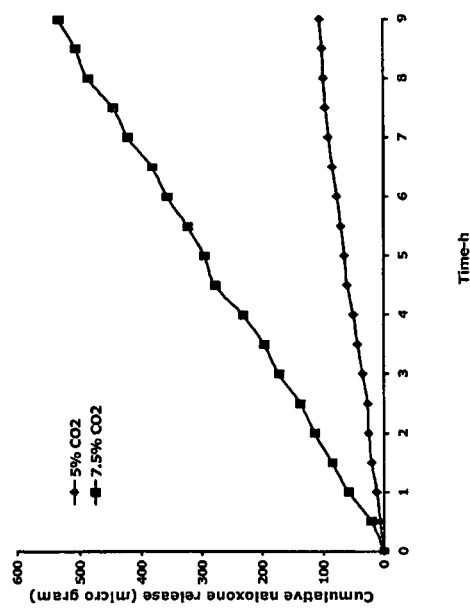
FIG. 7 shows the time and $CO_2$-responsive release of naloxone from a THPMA-EGDA hydrogel.

$CO_2$, the release of the entrapped naloxone is significantly slower as only 18% of the encapsulated naloxone is released after 12 hours (FIG. 7). The observed naloxone release profile at 7.5% $CO_2$ is significant because the $CO_2$ percentage during hyperventilation is in the range of 7.2-7.5%. In this range of % $CO_2$ the hydrogel starts to degrade most effectively, thereby allowing the release of the loaded naloxone.

Summary: The time- and $CO_2$-dependent release of naloxone in response to two different percentages of $CO_2$ (5 and 7.5%) was due to hydrolysis of $CO_2$-labile bond in THPMA at 7.5% $CO_2$, whereas at 5% $CO_2$ the acid labile monomer remained largely intact, thus the release is significantly slower.

EXAMPLE 4

Nanogel Preparation by Inverse Emulsion Polymerization

Figure 8:
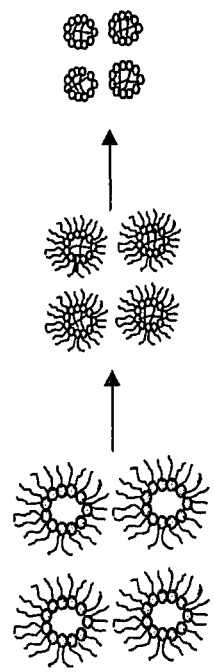
FIG. 8 illustrates the production of nanometer-sized loaded gel particles.

Inverse emulsion polymerization offers an efficient method to translate some of these controlled release approaches to spherical gel particles of nanometer size (FIG. 8). Tween-80 (polyethyleneglycol-sorbitan monooleate) and Span-80 (sorbitan monooleate) are employed as cosurfactants to obtain an optimal hydrophile lipophile balance, and both are FDA approved.

Poly(Acrylamide acetal-HEMA) based nanogel for the controlled and $CO_2$ dependent release of naloxone

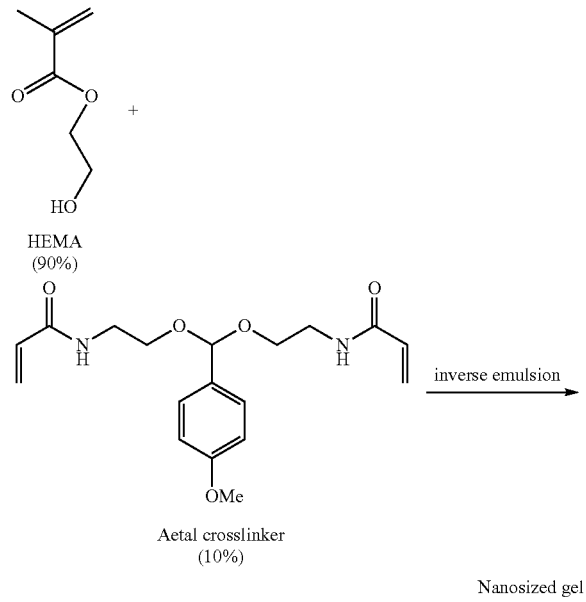

Scheme 3. Acid-degradable poly(acrylamide acetal-HEMA) nanogel.

Synthesis of nanogel by inverse emulsion polymerization: Inverse microemulsion polymerization was employed to produce $CO_2$-labile poly(acrylamide acetal-HEMA) nanogel (Scheme 3). The monomer HEMA (2-Hydroxyethyl methacrylate) was selected because it is water-soluble and possesses a low toxicity. A $CO_2$-labile bisacrylamide acetal crosslinker was synthesized by following the literature-reported method. The inverse emulsion polymerization procedure is briefly as follows: the organic phase of the polymerization contained of 5 mL of hexane with 150 mg of a 3:1 weight ratio of Span 80 (sorbitan monooleate) and Tween 80 (polyethyleneglycol-sorbitan monooleate). The aqueous phase of the polymerization included 0.5 mL of 0.1M PBS buffer at pH 8.0 containing a 10:90 mole ratio of acetal crosslinker (50 mg) and HEMA (168 mg) and 12 mg of the free radical initiator ammonium peroxodisulfate. The aqueous and organic phases were deoxygenated with argon. An inverse emulsion between the organic and aqueous phases was formed by mixing them and then sonicating for 30 seconds. Polymerization of the inverse emulsion was then initiated while stirring with a magnetic bar by adding 10 μL of N,N,N',N'-tetramethylethylene diamine. The stirred polymerization was allowed to proceed for 10 min at room temperature.

Encapsulation of naloxone in $CO_2$-labile nanogels: Encapsulation of naloxone was carried out via inverse emulsion polymerization following the same procedure as described above except that the inverse microemulsion is formed with an aqueous stock solution containing 10 mg of naloxone.

Purification of nanogels: The crosslinked nanogels were purified as follows: the suspension was transferred to a centrifuge tube. The washing process was carried out to remove the surfactants. Acetone and n-hexane at a volume ratio of 1:1 were chosen as the solvent as the surfactant is fully soluble in this mixture of solvents. To completely remove the surfactant, the mixture was centrifuged at 15,000 rpm for 10 minutes several times. Repeated centrifugation and washing removed virtually all surfactant and acetone-soluble species including unreacted monomers. The precipitate was then dried in a vacuum oven at 30° C. for 12 hours to yield the nanogels.

Characterization of nanogels: DLS. Dynamic light scatting is employed to analyze nanogel size and size distribution. The hydrodynamic sizes of nanogels were measured in deionized water. The mean effective diameter and polydispersity were determined. The temperature was kept constant at 25° C. throughout the experiment. Dust was eliminated by filtering the solution through a 0.25 μM filter. Briefly, 5-6 mg of nanogel was placed into a cuvette containing 2 mL of deionized water. Under the conditions described in this study, nanogels with diameters of 10-150 nm were obtained. The measurement was carried out three times and the average values are used. The size of nanogels nearly doubled, compared to the same polymerization reaction without naloxone

EXAMPLE 5

Poly(THPMA-co-HEMA-co-EGDA) based nanogel for the controlled and $CO_2$ dependent release of naloxone Scheme 4. Acid-degradable poly(THPMA-HEMA) nanogel

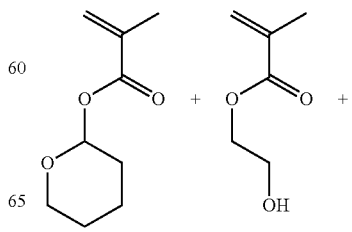

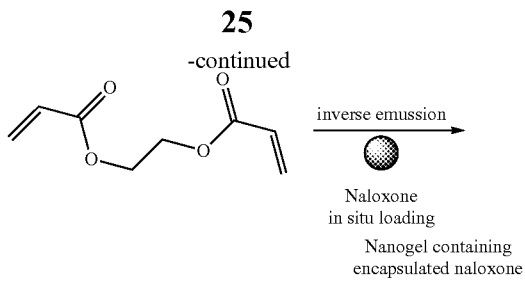

Synthesis of nanogel by inverse emulsion polymerization: Polymeric nanogels composed of THPMA-HEMA-EGDA were also synthesized by means of inverse emulsion system at room temperature by the free-radical polymerization method. In a typical route for nanohydrogel synthesis, microemulsion stock solutions are prepared by mixing 5 mL of hexane stock solution, which contains Tween-80 (70 mg) and Span-80 (75 mg) with an aqueous stock solution, which contains HEMA (23 mg), THPMA (180 mg), EGDA (35 mg), 12 mg of the free radical initiator ammonium peroxodisulfate, and water (0.5 mL of pH=8.0 PBS buffer) in a 20 mL glass vial followed by homogenization until an optically transparent solution was obtained. Afterward, the vial was covered with rubber septum, and the contents were flushed with argon for 15 minutes to remove the dissolved oxygen while stirring at room temperature. An inverse emulsion between the organic and aqueous phases was formed by mixing them and then sonicating for 30 seconds. Polymerization of the inverse emulsion was then initiated while stirring with a magnetic bar by adding 10 μL of N,N,N',N'-tetramethylethylene diamine. The stirred polymerization was allowed to proceed for 10 minutes at room temperature. During the polymerization reaction, the fluid became increasingly turbid, which is indicative of nanogel formation.

Encapsulation of naloxone in $CO_2$-labile nanogels: Encapsulation of naloxone was carried out via inverse emulsion polymerization following the same procedure as described above except that the inverse microemulsion is formed with an aqueous stock solution containing 10 mg of naloxone.

Purification of nanogels: The crosslinked nanogels were purified as follows: the suspension was transferred to a centrifuge tube. The washing process was carried out to remove the surfactants. n-Hexane and acetone at a volume ratio of 1:1 was chosen as the solvent as the surfactant is fully soluble in this mixture of solvents. To completely remove the surfactant, the obtained mixture was centrifuged at 15,000 rpm for 10 minutes several times. Repeated centrifugation and washing removes virtually all surfactant and acetone-soluble species including unreacted monomers. The precipitate was then dried in a vacuum oven at 30° C. for 2 hours to yield the nanogels.

Determination of drug loading efficiency: Naloxone encapsulation efficiency was determined by measuring the amount of free drug remained in the supernatant solution, not in the nanogel after collection of nanospheres by centrifugation. The amounts of free naloxone in the supernatant were measured using the UV absorbance at 281 nm. Encapsulation efficiency (EE, %)=(the amount of drug entrapped in the nanogel)/(the actual amount of drug used)×100; where the actual amount of drug used=the initial amount of drug used– the loss of drug during overall double emulsion procedures (in the absence of polymer).

Drug release experiment: The in vitro drug release was carried out at 37° C. as in Example 1 except the amount of gel taken for release study was 20 mg and the amount of naloxone encapsulated was 550 μg. The results are presented in terms of cumulative release as a function of time. The concentration of the drug is calculated from the corresponding calibration curve of the absorption against drug concentration. From this value, the amount of drug released at the selected time is estimated. The percent release is defined as the ratio of the concentration of naloxone in the hydrolyzed supernatant compared to that found in the completely hydrolyzed supernatant solutions (i.e., measured naloxone mass/naloxone loading mass).

Figure 9:
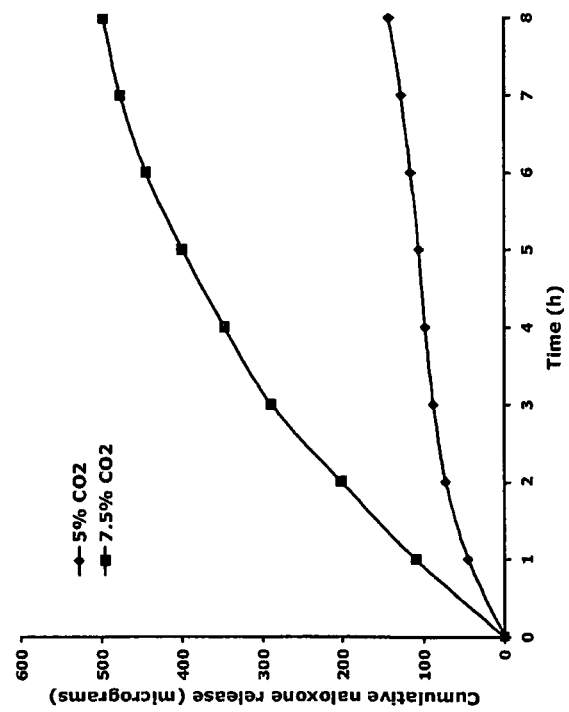
FIG. 9 shows the time and $CO_2$-responsive release of naloxone from a THPMA nanogel.

Drug release profile: The release of naloxone from the naloxone loaded hydrogel was evaluated as time- and % $CO_2$— dependent profiles shown in FIG. 9. The drug release from THPMA based nanogels at 5% $CO_2$ is very slow. Only about 20% of encapsulated naloxone was released after 8 hours (FIG. 9). Conversely, drug release from the nanogel at 7.5% $CO_2$ was significantly faster with about 95% of encapsulated drug releasing within the same time window. This faster release could be attributed to degradation of nanogel at 7.5% $CO_2$ and such degradation of the nanogels could trigger controlled release of encapsulated naloxone. These experimental results demonstrated that acid labile THPMA nanogels differentially release their payload under different percentages of $CO_2$. The profiles of drug release change greatly upon 5 and 7.5% $CO_2$ alteration. The drug release is carried out for 8 hours and the data in FIG. 5 showed that the drug is released quickly from the nanogel within the initial 1-2 hours at 7.5% $CO_2$, then the release rate slowed down and the drug release almost completed within 8 hours. The drastically increased drug release at 7.5% is attributed to the degradation of acetal group induced by pH changes created by 7.5% $CO_2$ and most of the loaded naloxone are squeezed out. The observed faster drug release from the nanogel can be explained by the higher surface area of the nanogels, compared to the bulk hydrogels. The drug release profile can be conveniently slowed down by increasing the crosslinking density of the nanogel. We estimate that increasing the crosslinker percentage to 30 to 60 mol % of the nanogel will provide complete control over the release profile. For example, a crosslinker percentage of about 10 mol % to 20 mol % will allow for release over 2 to 4 hours, relatively fast release, while we anticipate that a crosslinker percentage of about 30 mol % to 60 mol % will allow release over 6 to 12 hours, that is, slow release.

Characterization of nanogels: DLS. Dynamic light scattering was employed to analyze nanogel size and size distribution. The hydrodynamic sizes of nanogels were measured in deionized water. The mean effective diameter and polydispersity were determined. The temperature was kept constant at 25° C. throughout the experiment. Dust was eliminated by filtering the solution through 0.25 μM filter. Briefly, 5-6 mg of nanogel was placed into a cuvette containing 2 mL of deionized water. Under the conditions described in this Example, nanogels with diameters of 10-150 nm were obtained. The measurement was carried out three times and the average values were used. Exemplary results are shown in FIG. 6a and FIG. 6b.

EXAMPLE 6

Poly(DMAEMA-co-THPMA-co-HEMA-co-EGDA) based hydrogel for the controlled and $CO_2$ dependent release of morphine Scheme 5. Synthesis of DMAEMA-THPMA-HEMA-EGDA based hydrogels.

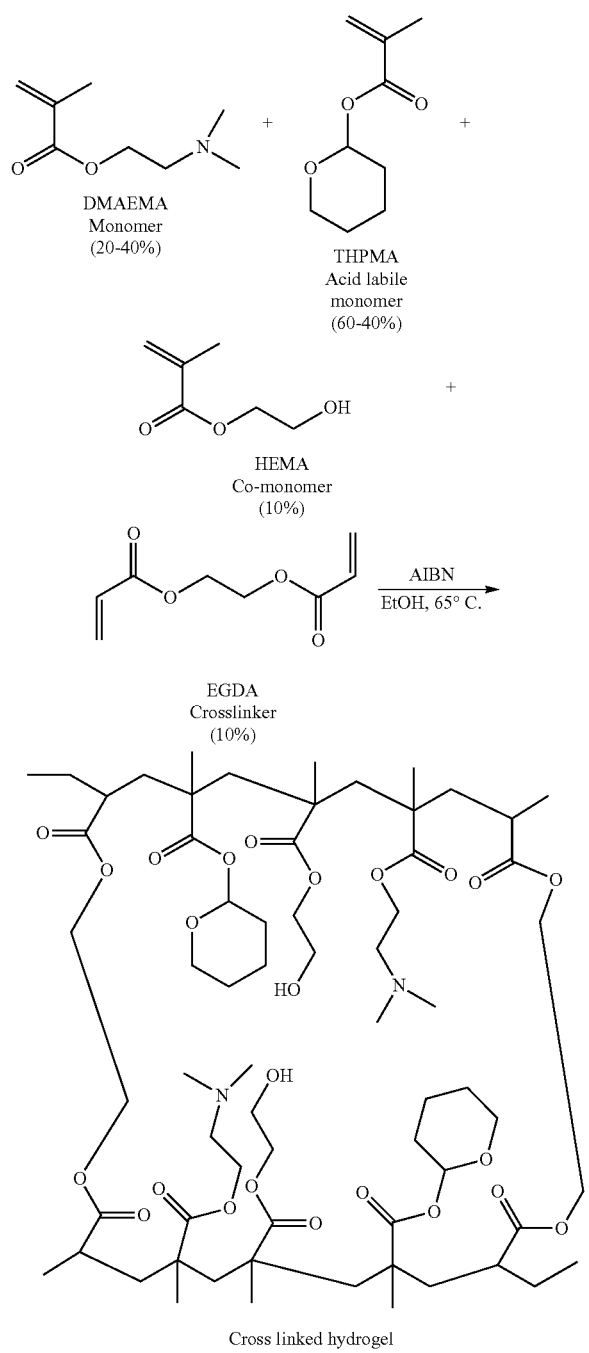

Cross linked hydrogel

Materials.

2-Dimethylamino methacrylate (DMAEMA), methacrylic acid (MAA), 3,4-dihydro-2H-pyran (DHP), 2-hydroxyethyl methacrylate (HEMA) and ethylene glycoldiacrylate (EGDA) were purchased from Aldrich and used as reactants in the synthesis of the hydrogel. Azobisisobutyronitrile (AIBN) was purchased from Aldrich and recrystallized in methanol prior to use. The chemical structures of the monomers and crosslinker are shown in Scheme 5. All other reagents and organic solvents were used as chemical grade. The therapeutically active substance, morphine, was supplied by Aldrich in the morphine sulphate pentahydrate dimer form and used without further purification. Its structure is:

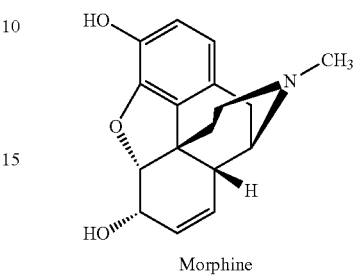

Morphine

Hydrogel synthesis by free-radical polymerization: THPMA (2-tetrahydropyranylmethacrylate) was synthesized by following literature reported method. A poly(DMAEMA-THPMA-HEMA-EGDA) based hydrogel was synthesized by free radical reaction of DMAEMA (positively charged monomer), THPMA ($CO_2$-labile monomer), HEMA (neutral co-monomer) and EGDA as crosslinker using AIBN as a free radical initiator. Briefly, DMAEMA, THPMA, HEMA and AIBN with particular mole ratios (Table 3) were placed in a Teflon-capped vial (20 mL), dissolved in ethanol (2 mL) and allowed to stir for 10 minutes. The resulting solution was degassed using argon gas flow for 15 minutes. After that the vial was heated to 70° C. to initiate radical reaction and allowed to stand for 24 hours to complete the cross-linking reaction. The formed hydrogel was then cooled to room temperature.

Purification of hydrogels: The hydrogels were first washed with diethyl ether many times to remove the unreacted THPMA and then kept in distilled water for 5 days to remove any impurities and unreacted species.

TABLE 3

Feed composition and % yields of polymerization and encapsulation.

| Hydrogel Composition (%) | Monomers (mg) | Cross-linker (mg) | Polymerization yield (%) | Morphine encapsulation efficiency (%) |
|---|---|---|---|---|
| GEL I-(20) | DMAEMA (167) THPMA (530) HEMA (60) | EGDA (95) | 92 | 65 |
| GEL II-(30) | DMAEMA (167) THPMA (300) HEMA (40) | EGDA (64) | 93 | 76 |
| GEL III-(40) | DMAEMA (167) THPMA (181) HEMA (30) | EGDA (48) | 95 | 83 |

Drug loading: Morphine, as a model drug, was loaded into the hydrogel by imbibition (solvent-sorption) method. For imbibition, the swollen gels (already soaked in distilled water for 2 hours) were soaked into a solution of morphine (5 mg in 2 mL deionized water) at 37° C., and allowed to swell to equilibrium (for at least 4 days) in order to get a high loading in the gel. The fully swollen hydrogels removed from the drug solution were blotted with filter paper to eliminate the surface water and dried at room temperature for 12 hours. The amount of the morphine loaded into the hydrogel was quantified by UV absorption at 283 nm in deionized water.

Encapsulation efficiency: To determine the encapsulation efficiency (EE %), the amount of un-loaded morphine after the drug loading was measured by the UV absorbance of the solution at 283 nm after removing the drug-loaded hydrogel. The encapsulation efficiency (EE %) is defined as: EE %=(feed amount of morphine)−(un-loaded amount of morphine)/feed amount of morphine×100%.

Drug release measurement: The in vitro drug release is carried out at 37° C. as in Example 1.

Figure 10:
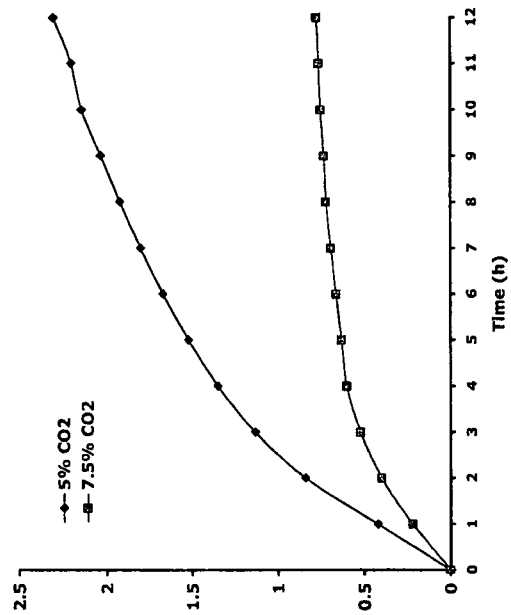
FIGS. 10-12 show $CO_2$-responsive morphine release from DMAEMA-THPMA-HEMA-EGDA hydrogels.
Figure 11:
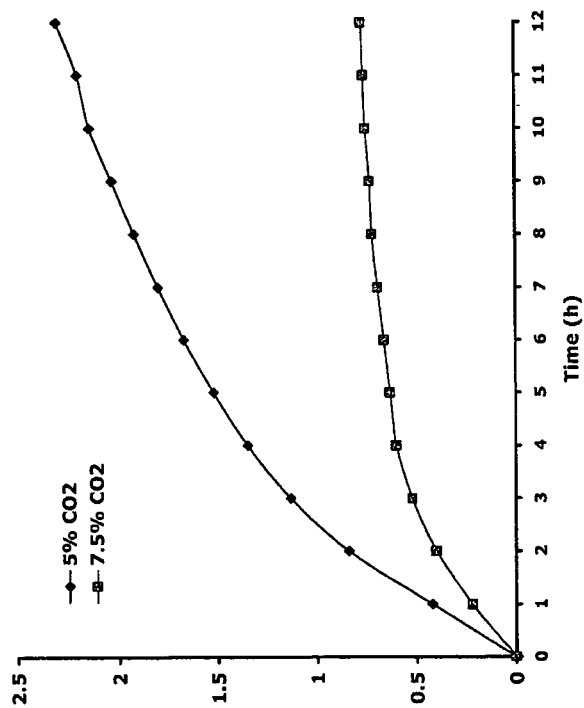
Figure 12:
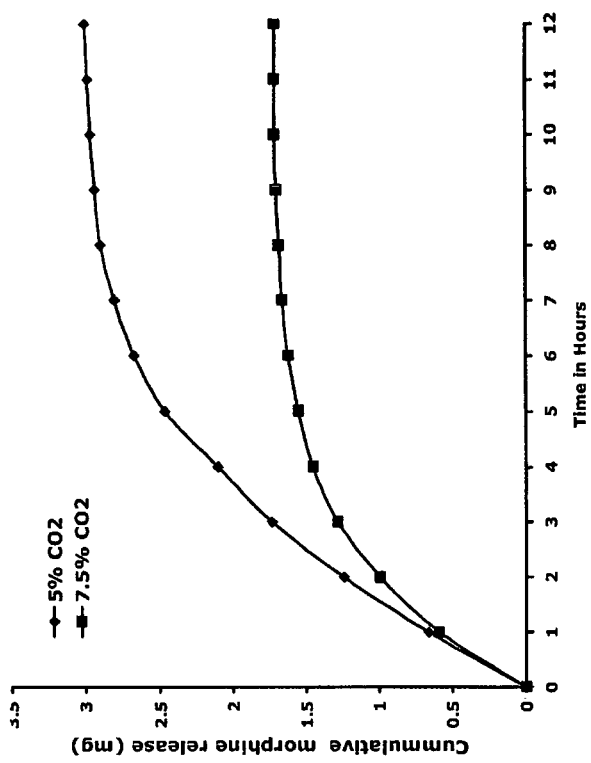

Drug release profile: FIGS. 10, 11 and 12 represent the 5% and 7.5% $CO_2$ dependent release profiles of morphine loaded hydrogels (20%, 30% and 40% respectively). In this system, the major factor controlling the release amount is the swelling which is expected at 5% $CO_2$ due to electrostatic repulsion between the positively charged amine moieties and shrinking of the hydrogel at 7.5% $CO_2$, which is effected by the degradation of the THPMA moiety followed by the electrostatic attraction between the positively charged amine and negatively charged carboxylate moieties. The profiles of drug release showed changes upon 5 and 7.5% $CO_2$ alteration with greater changes observed for the 20% composition. These experimental results demonstrate that DMAEMA-THPMA-HEMA-EGDA based hydrogel differentially release their payload under different percentages of $CO_2$. The drug release is carried out for 12 hours for all three compositions and the data are shown in FIGS. 10, 11 and 12. The DMAEMA density is arranged in a sequence of Gel I<Gel II<Gel III, the controlled and 5% and 7.5% $CO_2$ dependent drug release rate is also arranged in the same order. Among the different hydrogels, Gel I has the highest controlled- and % $CO_2$-dependent release rate because of it has the lowest DMAEMA density.

Summary: The release of morphine from these gels in response to two different percentages of $CO_2$ (5 and 7.5%) is dominated by the magnitude of swelling and shrinking in the hydrogel. The release profile showed significant changes with respect to 5% and 7.5% $CO_2$.

EXAMPLE 7

Acrylic Acid Based Gel for the Controlled Release of Morphine

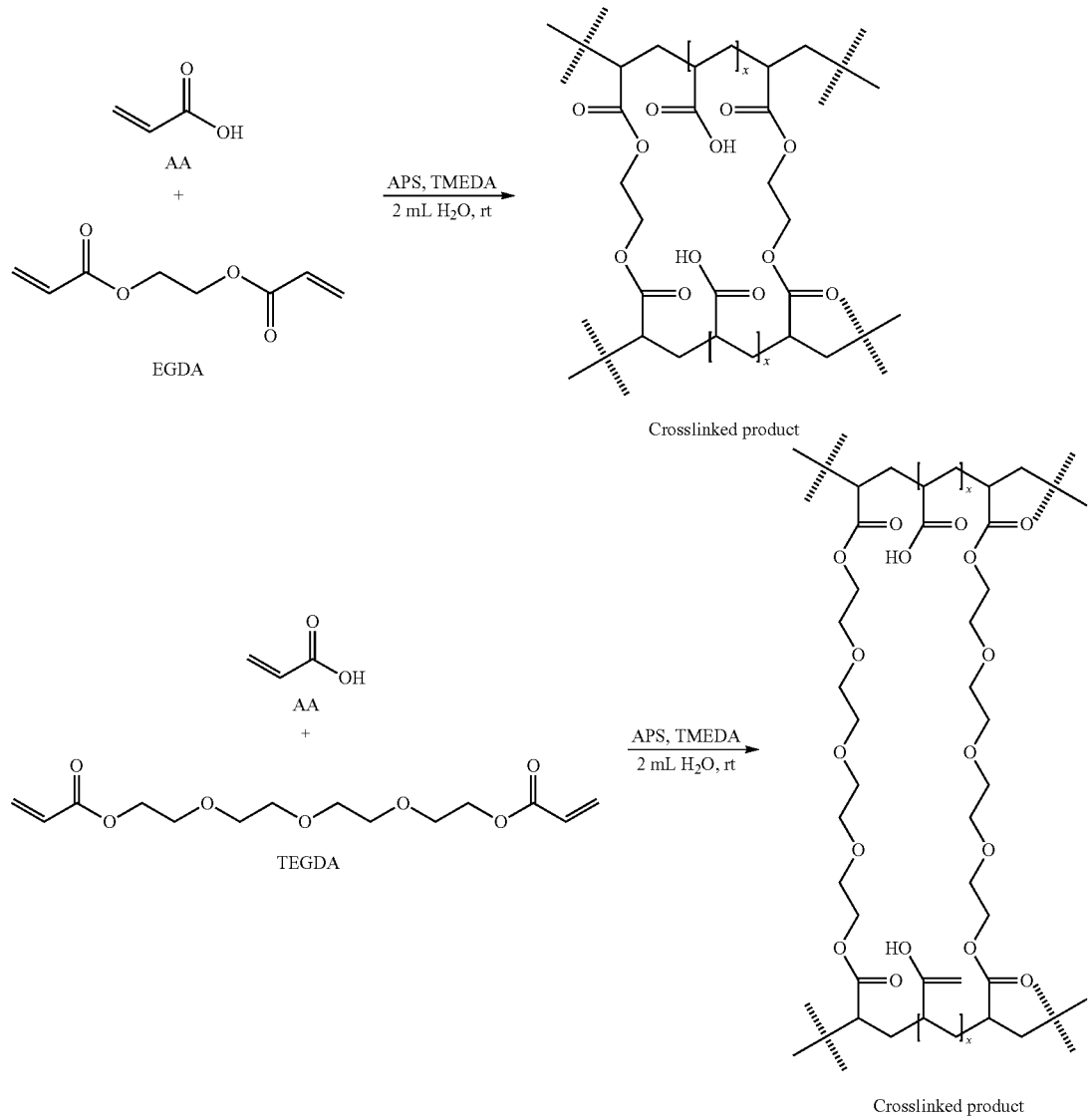

Scheme 7. NaAA: EGDA gel and NaAA: TEGDA
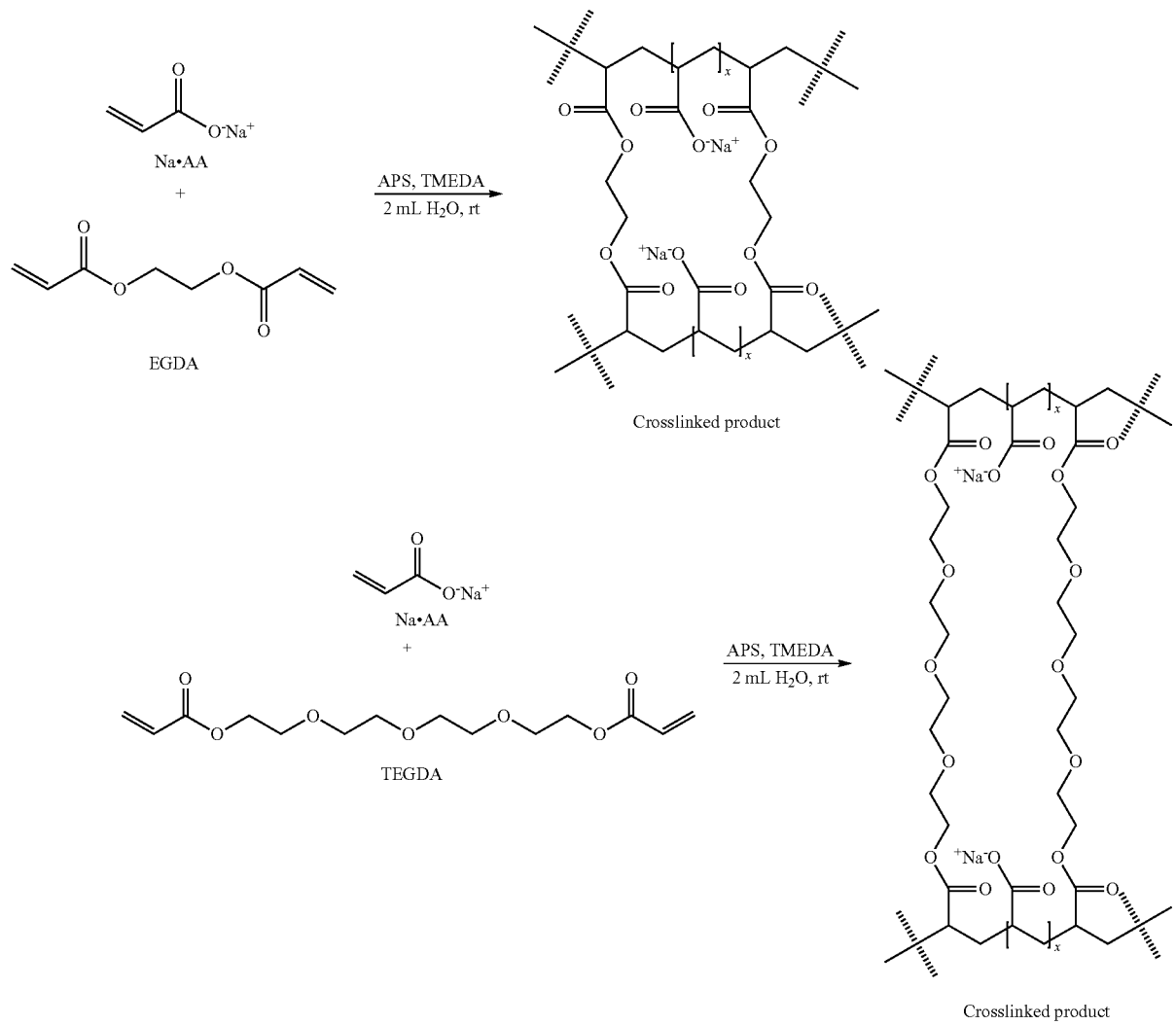
Hydrophobically Modified AA Gels
Scheme 8. AA: BA: EGDA gels
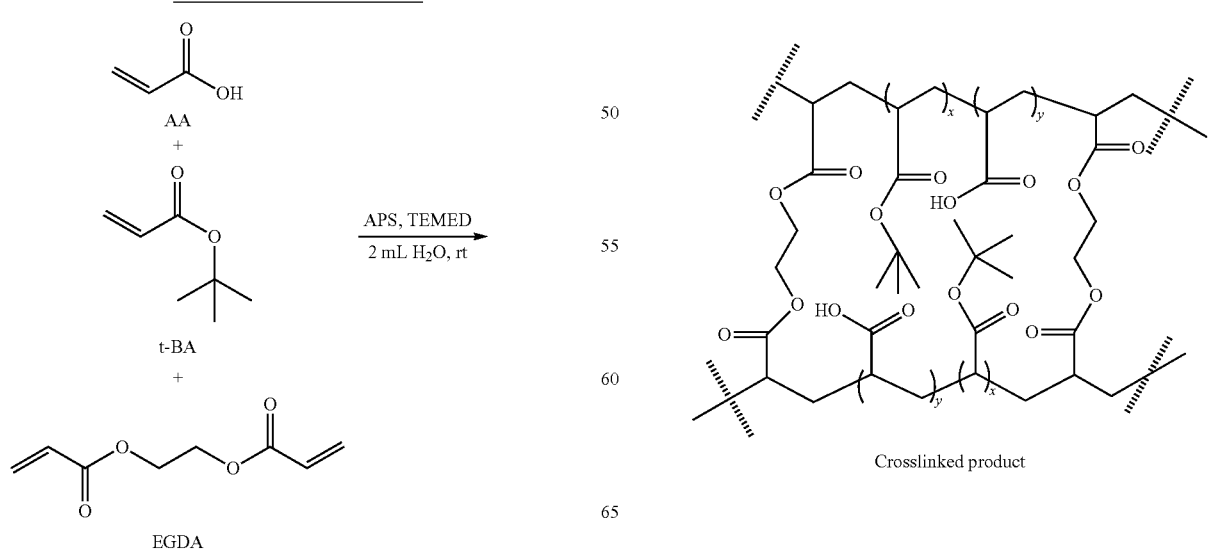
-continued Scheme 9. AA: HEMA: EGDA
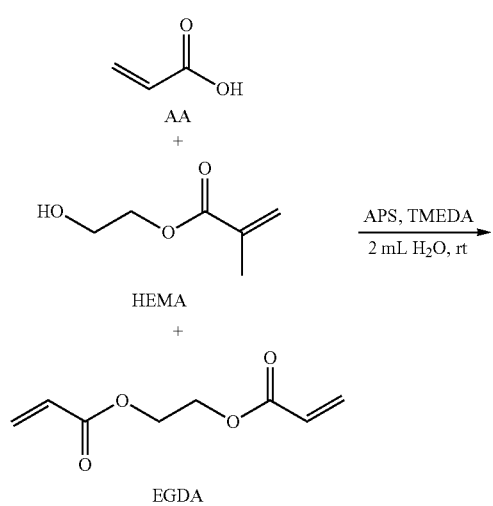
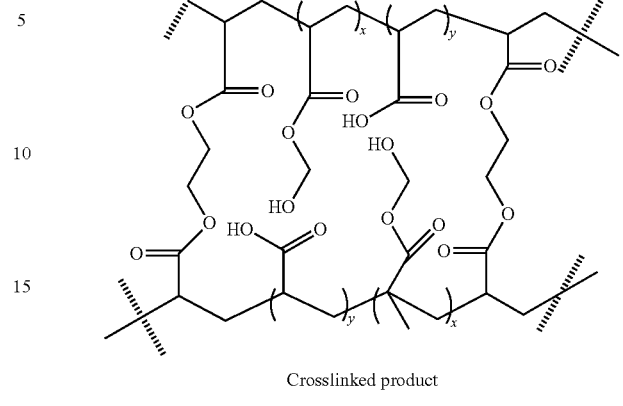
Gels by Chemical Mixing
Scheme 10. AA: NaAA: TEGDA
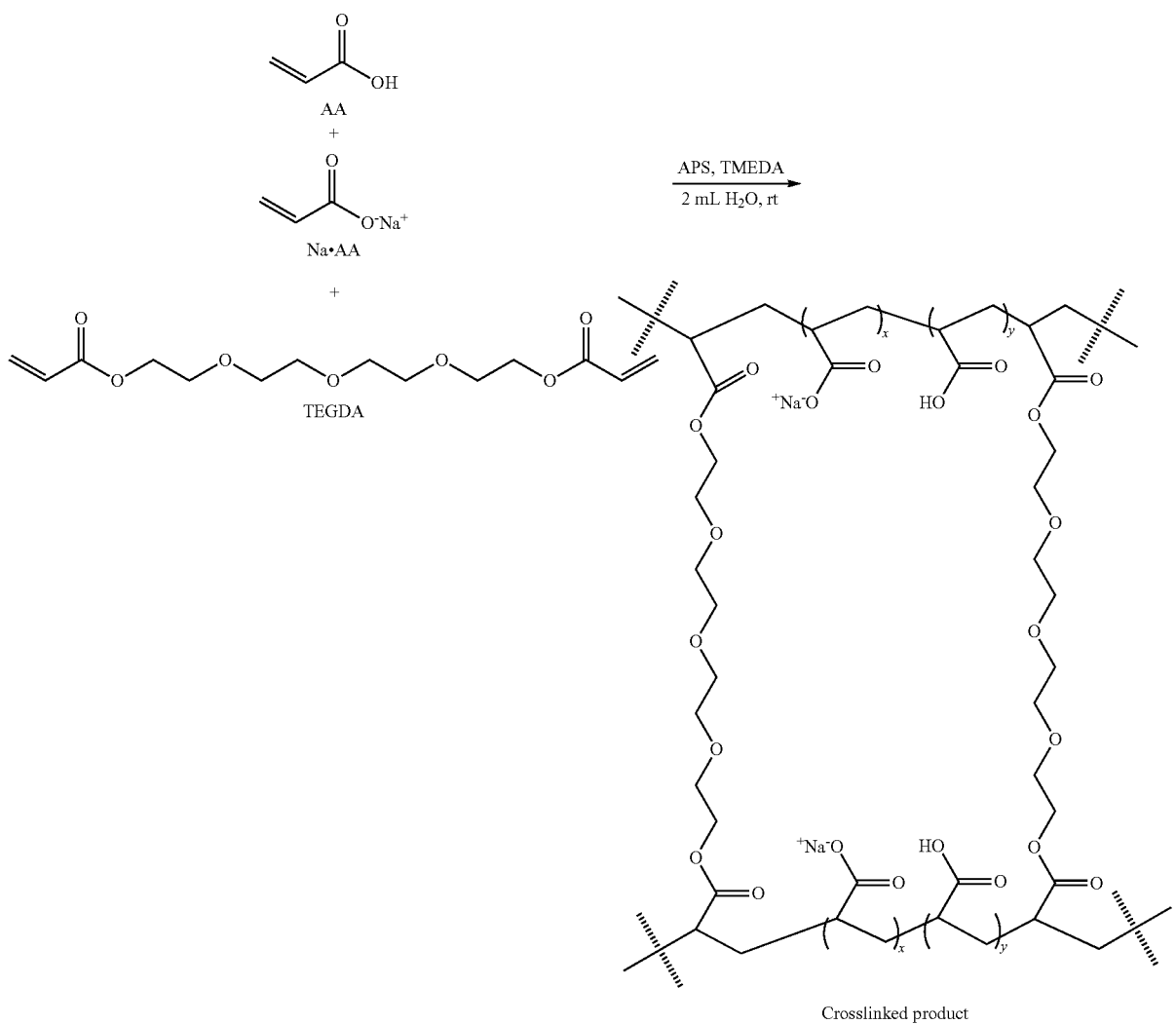

Scheme 11. AA: EGDA + NaAA: EGDA

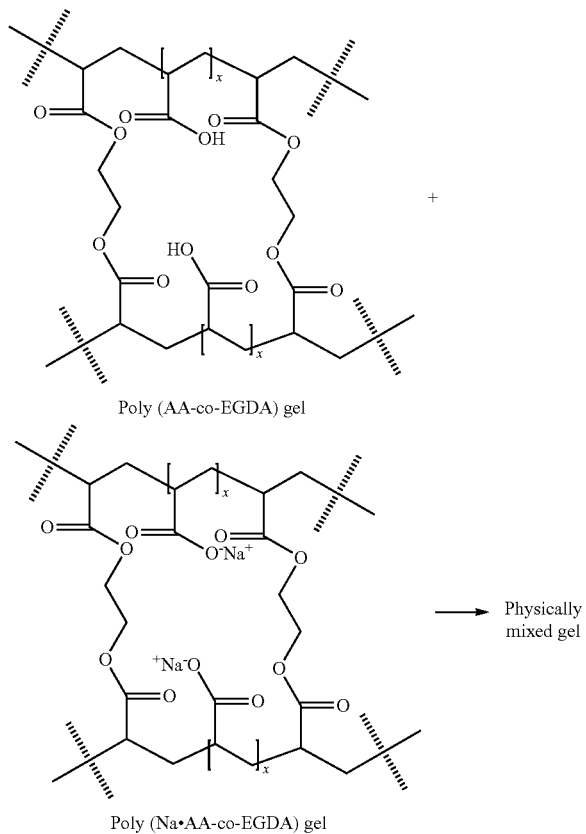

Poly (AA-co-EGDA) gel

Poly (Na•AA-co-EGDA) gel

→ Physically mixed gel

Abbreviations:
Functional Monomers
AA: Acrylic acid
NaAA: Sodium salt of acrylic acid
HEMA: 2-hydroxyethyl methacrylate
t-BA: t-Butyl acrylate
Cross-Linkers
EGDA: Ethylene glycol diacrylate
TEGDA: Tetraethylene glycol diacrylate
Initiator
APS: Ammonium persulphate
Catalyst
TEMED: N,N,N',N'-tetramethylethylene diamine
Solvent
$H_2O$: Water
EtOH: Ethanol Hydrogel synthesis: All the hydrogels were synthesized by free-radical bulk polymerization using APS as a free radical initiator and TEMED as a catalyst.

AA:EGDA: The monomer AA (1 mL, 14.5 mM) and cross-linker EGDA (0.1 mL, 0.64 mM) were dissolved in 2 mL deionized water. The AA/EGDA mole ratio was approximately 95/5. The reaction mixture was degassed prior to polymerization. Then, 100 µL of APS (the initiator) (APS stock 2 g in 2.5 mL water) and 100 µL of TEMED (the catalyst) were added to the reaction mixture. After mixing thoroughly, the solution is allowed to stand at room temperature for polymerization. Hydrogel formation was observed within 10 min of reaction time. After completion of reaction time the hydrogel was washed with deionized water for two days.

Similarly other gels, i.e., AA: TEGDA, AA: t-BA: EGDA, AA:MMA:EGDA were prepared by varying the co-monomer compositions and purified.

NaAA:EGDA: The monomer AA (1 mL, 14.5 mM), cross-linker EGDA (0.1 mL, 0.64 mM) and sodium hydroxide (0.56 gm, 14 mM) were dissolved in 2 mL deionized water. The NaAA/EGDA mole ratio was approximately 95/5. The reaction mixture was degassed prior to polymerization. Then, 140 µL of APS (the initiator) (APS stock 2 g in 2.5 mL water) and 100 µL of TEMED (the catalyst) are added to the reaction mixture. After mixing thoroughly, the solution was allowed to stand at room temperature for polymerization. Hydrogel formation was observed within 10 minutes of reaction time. After completion of reaction time the hydrogel was washed with deionized water for two days.

Similarly other gels, e.g., NaAA:TEGDA were prepared and purified.

Chemical mixing of AA gels (AA:Na.AA:EGDA): Chemically mixed gels were prepared by varying the amount of sodium hydroxide during the hydrogel synthesis.

TABLE 4

Amount of monomer (AA), cross-linker (EGDA) and sodium hydroxide used for polymerization of chemically mixed gels

| AA (mM) | EGDA (mM) | NaOH (mM) | Ratio AA:Na.AA:EGDA |
|---|---|---|---|
| 14.5 | 0.64 | 10.5 | 20:75:5 |
| 14.5 | 0.64 | 7.00 | 45:50:5 |
| 14.5 | 0.64 | 3.50 | 70:25:5 |
| 14.5 | 0.64 | 1.40 | 85:10:5 |

Physically mixed AA gels (AA:EGDA and Na.AA:EGDA): In this example, separately synthesized AA and sodium acrylate gels loaded with morphine are mixed together in various ratios and the drug release profile was studied.

General method drug loading: Morphine was loaded into the hydrogel by imbibition (solvent-sorption) method. The swollen gels (already soaked in distilled water for 12 hours) were soaked into a solution of morphine at 37° C., and allowed to swell to equilibrium in order to get a high loading in the gel. The fully swollen hydrogels removed from the drug solution were blotted with filter paper to eliminate the surface water and dried at room temperature. The loading amount of drug can be adjusted by controlling the concentration of drug solution.

Figure 13:
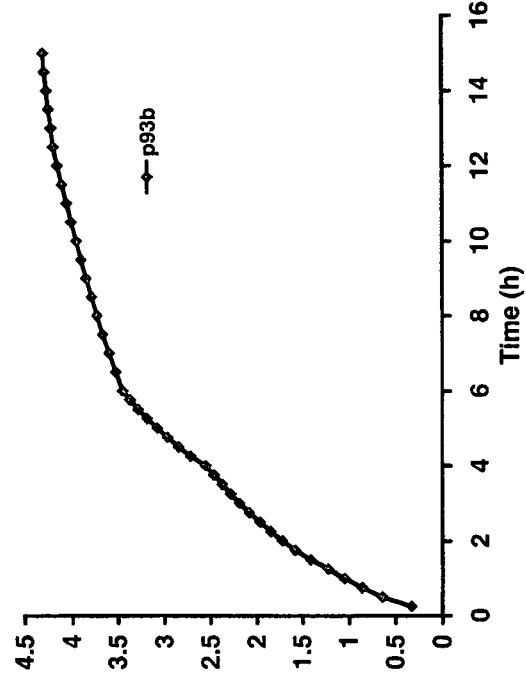
FIG. 13 shows a release profile for morphine from an acrylic acid gel.
Figure 14:
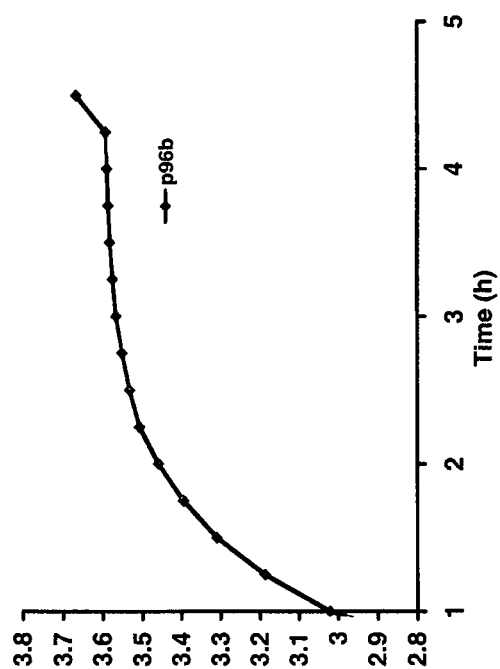
FIG. 14 shows a release profile for morphine from a sodium salt of acrylic acid gel.

General method for drug release under varied $CO_2$ content: Morphine release study experimental set up. The drug-loaded hydrogels (a certain measured amount being same for all % $CO_2$) were taken in small vials. 1 or 2 mL PBS buffer of 7.4 pH is added and $CO_2$ was purged through the manifolds into the vial, covered by a septum through a needle having another needle as the outlet. The rate of purging was about 1 bubble per second on average. After frequent time intervals (15 minutes or 30 minutes), all the solution was taken out and fresh 1 ml PBS buffer was added to the hydrogels. This process was continued for 3-12 hours depending on the type of hydrogels. The calculation of the total amount of drug released at a given time was calculated by UV absorbance at that particular time interval and all the released amounts added to find out the cumulative release. Release profiles are shown in FIG. 13 for a 95:5 AA:EGDA hydrogel and FIG. 14 for a 95:5 NAA:EGDA hydrogel.

Figure 15:
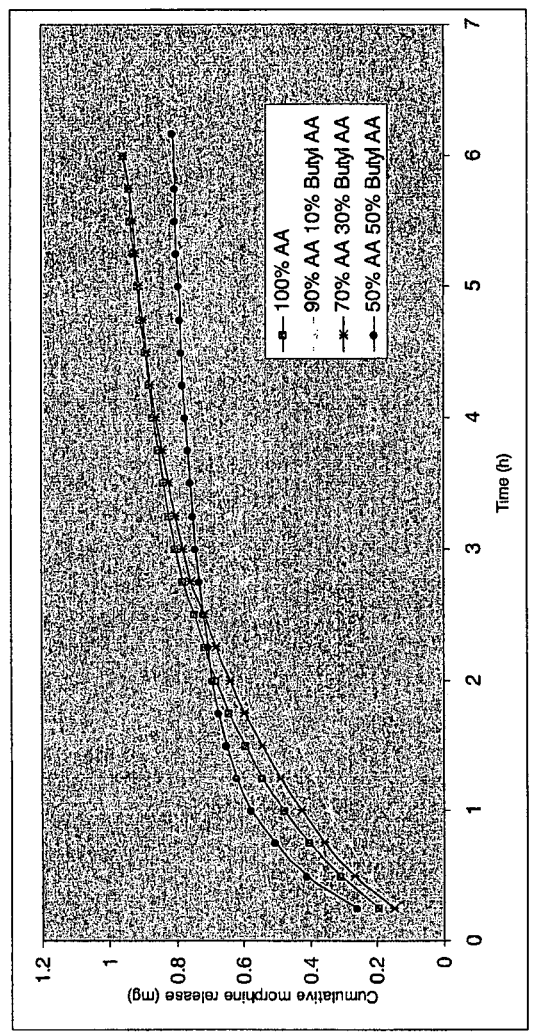
FIGS. 15-16 show release profiles for morphine from hydrophobically modified acrylic acid hydrogels.
Figure 16:
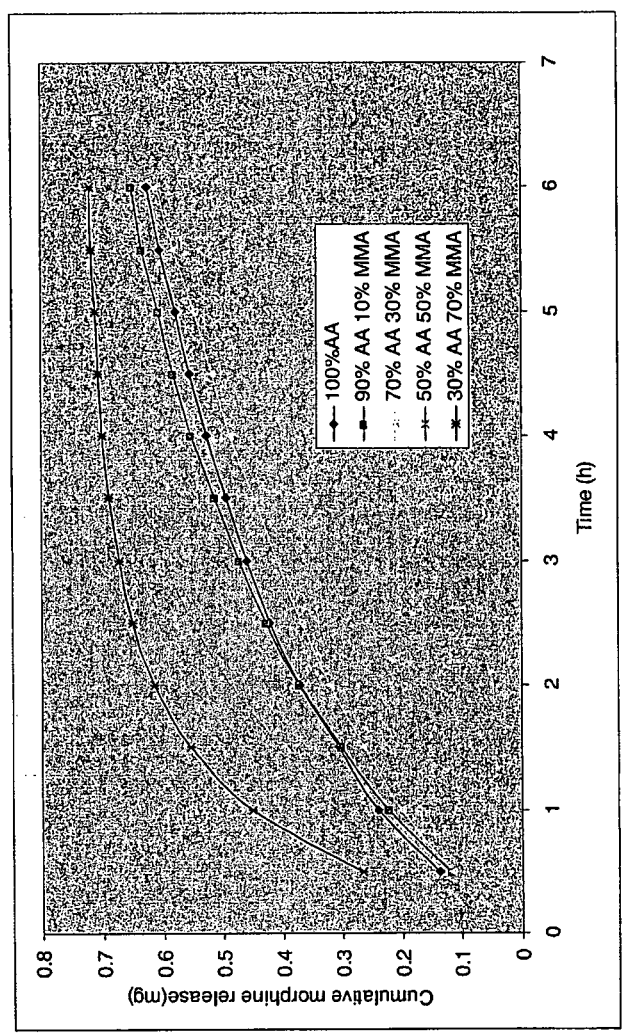

Hydrophobically modified AA gels: Tunable morphine release profiles are observed depending on the hydrophobicity and hydrophilicity balance in the gel. Results are shown in FIG. 15 and FIG. 16.

Figure 17:
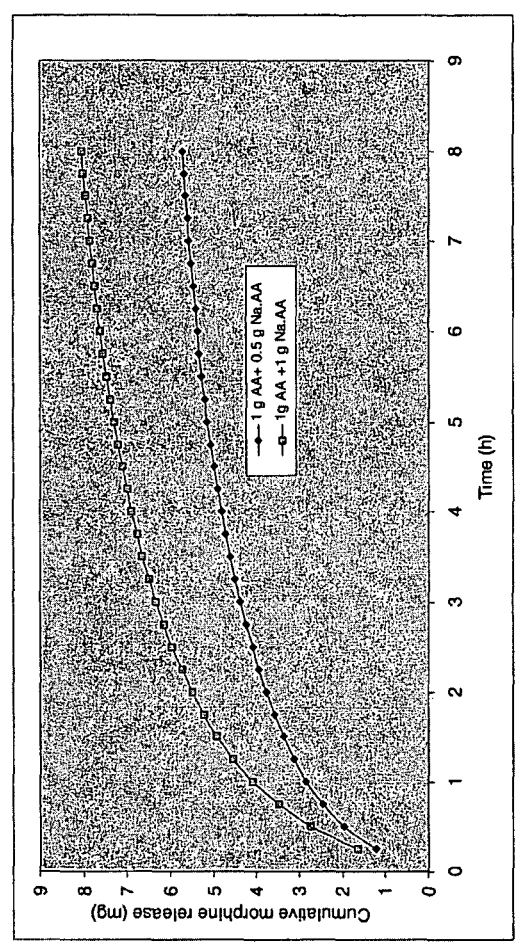
FIG. 17 shows release of morphine from physically mixed acrylic acid and sodium salt of acrylic acid hydrogels.

Physically mixed gels Results are shown in FIG. 17 for mixed acrylic acid and methacrylic acid hydrogels.

EXAMPLE 8

Poly(IA-co-HEMA-co-EGDA) Based Hydrogel for the Controlled and $CO_2$ Independent Release of Morphine Scheme 12. Synthesis of IA-HEMA-EGDA based hydrogel.

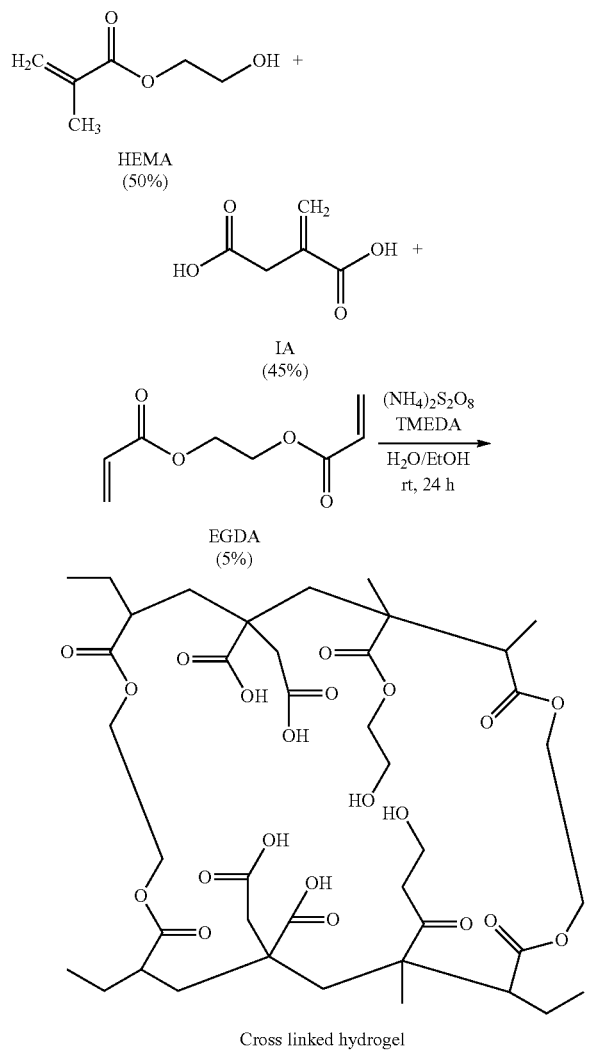

Materials: Itaconic acid (IA), 2-hydroxyethyl methacrylate (HEMA) and ethylene glycoldiacrylate (EGDA) were purchased from Aldrich and used as reactants in the synthesis of the hydrogel. The HEMA monomer was distilled, under vacuum, prior to use. Ammonium persulfate (APS) and N,N, N',N'-tetramethylethylene diamine (TMEDA) were purchased from Acros Organics USA, Morris Plains, N.J., and used without further purification. The chemical structures of the monomers and crosslinker are given in Scheme. 12. Water was purified using the Milli-Q system (Millipore). The therapeutically active substance, morphine, was supplied by Aldrich as morphine sulphate pentahydrate in dimer form and used without further purification.

Hydrogel synthesis by free-radical polymerization: The hydrogel based on the monomers: IA, HEMA, and the crosslinker: EGDA was prepared using the following steps. IA (840 mg, 6.45 mmol), HEMA (932 mg, 7.16 mmol) and EGDA (122 mg, 0.72 mmol) were dissolved in 2 mL of a water/ethanol mixture (1:1, by volume). The HEMA/IA/EGDA mole ratio was 50/45/5. The reaction mixture was degassed prior to polymerization. Then, 10 μL of a 50% ammonium persulphate solution (the initiator) and 10 μL of N,N,N',N'-tetramethylethylene diamine (the accelerator) were added to the reaction mixture. After mixing thoroughly, the solution was allowed to stand for 24 hours to complete the polymerization/cross-linking reaction at room temperature.

Purification of hydrogels: The hydrogels were kept in distilled water to remove any impurities and unreacted species. The yield of polymerization is 92%.

Drug loading: Morphine, as a model drug, was loaded into the hydrogel by imbibition (solvent-sorption) method. For imbibition, the swollen gels (already soaked in distilled water for 1 hour) were soaked into a solution of morphine (5 mg in 2 mL deionized water) at 37° C., and allowed to swell to equilibrium in order to get a high loading in the gel (at least for 2 days). The fully swollen hydrogels removed from the drug solution were blotted with filter paper to eliminate the surface water and dried at room temperature for 12 hours. The amount of the morphine loaded into the hydrogel is quantified by UV absorption at 283 nm in deionized water.

Encapsulation efficiency: To determine the encapsulation efficiency (EE %), the amount of un-loaded morphine after the drug loading was measured by the UV absorbance of the solution at 283 nm after removing the drug-loaded hydrogel.

The encapsulation efficiency (EE %) is defined as: EE %=(feed amount of morphine)−(un-loaded amount of morphine)/feed amount of morphine×100%. The loading efficiency and loading capacity of morphine into the hydrogel was found to be 85%, based on the initial amount of morphine, and 30 mol %, respectively, as determined by the LTV measurement. This method has advantages over the simultaneous method in which the drug is incorporated during polymerization (in situ), that is, the unreacted materials can be removed before drug loading and the loading amount of the gel can be adjusted by controlling the concentration of drug solution.

Drug release measurement: The amount of drug released was analyzed at each time point in response to two different percentages (5 and 7.5%) of $CO_2$ as in example 1. The amount of swollen gel taken for release study was 100 mg and the amount of morphine loaded in 100 mg of the swollen gel was 2.6 mg. The results are presented in terms of cumulative release as a function of time. The concentration of the drug was calculated from the corresponding calibration curve of the absorption against drug concentration. From this value, the amount of drug released at the selected time was estimated. All promising releasing experiments were performed in duplicate or triplicate.

Figure 18:
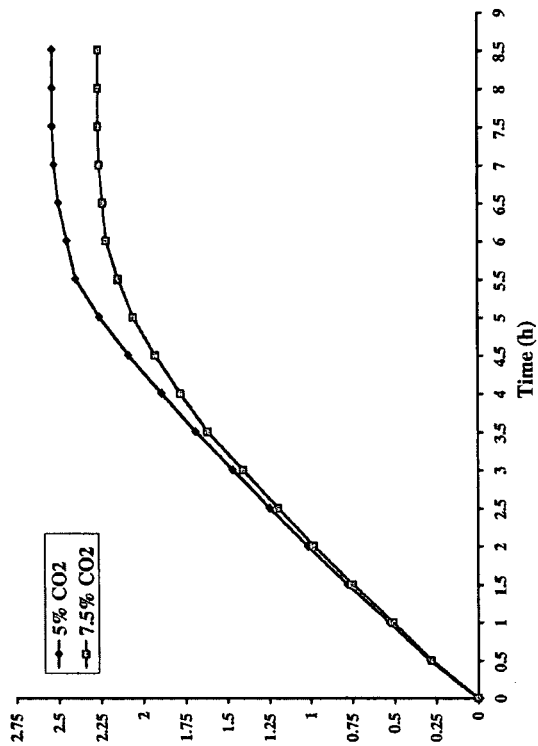
FIG. 18 shows the 5% and 7.5% $CO_2$ dependent release profiles from a morphine loaded hydrogel, wherein the hydrogel contains itaconic acid to increase the hydrophilicity of the gel.

Drug release profile: FIG. 18 represents the 5% and 7.5% $CO_2$ dependent release profiles from morphine loaded hydrogel. In this system, the major factor for controlling the release amount is the swelling of the hydrogel affected by the surrounding pH, which in turn is influenced by 5 and 7.5% $CO_2$. Morphine is expected to diffuse through the water swelling region in the polymer gel. A controlled release rate of about 0.4 mg/hour for 5-6 hours is observed and 94% of encapsulated morphine was released within this time window. The controlled release presumably occurred by the pore diffusion mechanism. Since there was no significant difference in release profile in response to 5 and 7% $CO_2$, it is considered that the release rate of morphine from IA based hydrogel is nearly independent of $CO_2$ percentages.

Swelling experiments: Dynamic swelling experiments were performed in buffer solutions of different pH at 37° C. (pH=7.4 and pH=5.2). Swollen gels removed from the swelling medium at regular intervals were dried superficially with filter paper, weighed and placed in the same bath. The measurements were continued until a constant weight was reached for each sample. The degree of swelling (q) is calculated using the following:

$$q=(W_t-W_0)/W_0, \quad (1)$$

where $W_0$ and $W_t$ are the weights of the hydrogel at time 0 and of the swollen hydrogel at time t, respectively.

The equilibrium degree of swelling ($q_e$) is calculated as follows:

$$q_e=(W_e-W_0)/W_0, \quad (2)$$

where $W_e$ is the weight of the swollen hydrogel at equilibrium. All swelling experiments were performed in triplicate.

Swelling/Degradation Study of Polyacrylamide Acetal-HEMA) Based Hydrogel

| % Crosslinker | pH | % Degradation/Swelling (after 24 h) |
|---|---|---|
| 10 | 4.3 | 33 (degradation) |
|  | 5.5 | 21 (degradation) |
|  | 6.4 | 15 (dedradation |
|  | 7.4 | 42 (swelling) |
| 15 | 4.2 | 54 (degradation) |
|  | 5.4 | 25 (degradation) |
|  | 6.2 | 18 (degradation) |
|  | 7.4 | 34 (swelling)) |

Weight Loss of Blank poly(HEMA-DVSDO) Hydrogel with Time upon Incubation in Phosphate Buffer at 37° C.

| % Crosslinker | pH | % Degradation (after 24 h) |
|---|---|---|
| 20 | 5.5 | 42 (degradation) |
|  | 7.4 | 2 (degradation) |

EXAMPLE 9

Methacrylic Acid and N-Methacryloyl Glutamic Acid Gels for Controlled Release of Morphine Reaction Schemes Scheme 13. MAA: TEGDA

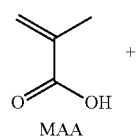
MAA

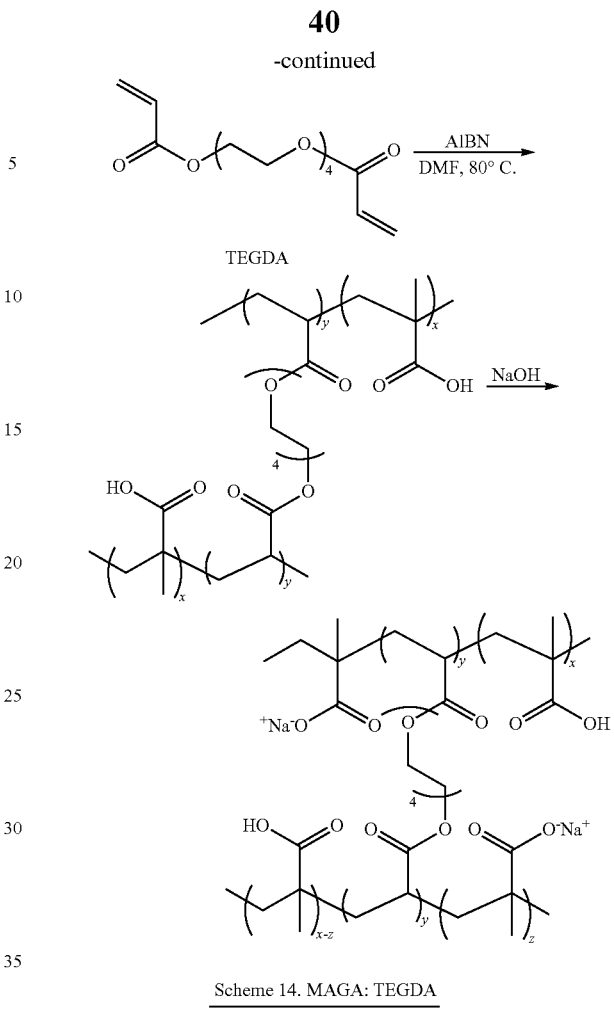

Scheme 14. MAGA: TEGDA

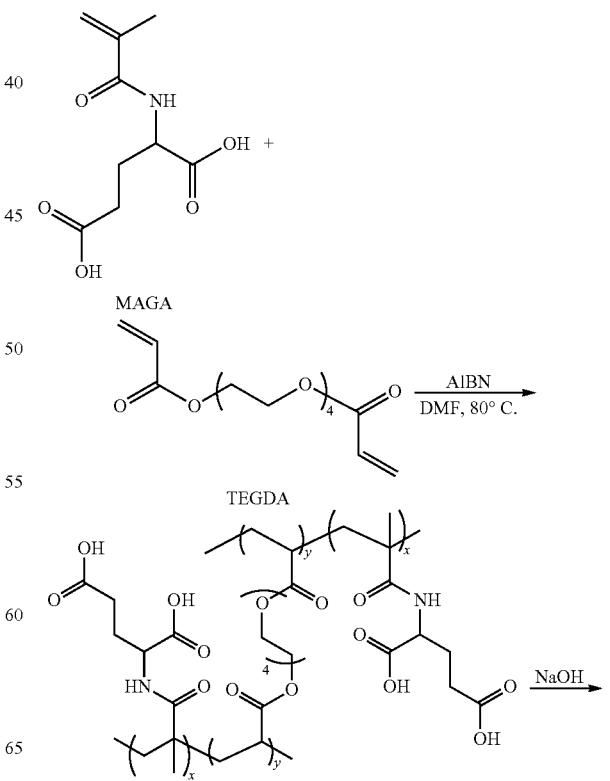

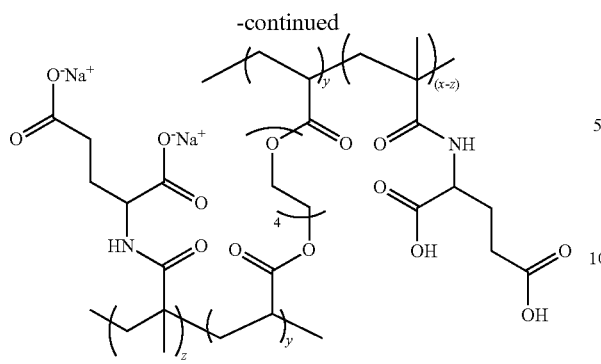

Abbreviations:
MAA—methacrylic acid
TEGDA—tetra(ethylene glycol) diacrylate
MAGA—N-methacryloyl glutamic acid
AIBN—azobisisobutyronitrile
DMF—dimethyl formamide
PBS—phosphate buffered saline Hydrogel synthesis: MAA: TEGDA. The monomer, MAA (1.6 mL, 19.0 mmol) and the cross-linker, TEGDA (0.27 ml, 1.0 mmol) were mixed together in 4 mL DMF as the solvent after which the initiator AIBN (0.03 g, 0.2 mmol) was added. The mixture was degassed with argon and heated at 80° C. for 4 hours to obtain a cross-linked polymeric network. After the polymerization, the product was cooled to ambient temperature and then washed with acetone for 3 days followed by distilled water to remove un-reacted monomer and cross-linker. The purity of the gels was determined by carrying out UV-vis spectroscopy on the supernatant solution from the washing. The absence of a peak at 250 nm signifies the purity of gel. These gels were further soaked in NaOH solution (pH=8) to neutralize the acid functionalities. A final pH of 6.5 was obtained after several wash with NaOH and then 1×PBS (pH=7.4). The gels were dried to constant weight.

MAGA: TEGDA: The synthesized monomer, MAGA (2.0 g, 9.5 mmol) and the cross-linker TEGDA (0.13 mL, 0.5 mmol) were mixed together in 4 mL DMF after which the initiator AIBN (0.02 g, 0.1 mmol) was added. The mixture was degassed with argon and heated at 80° C. for 4 hours to obtain a cross-linked polymeric network. After the polymerization, the product was cooled and then washed with NaOH (pH=8.0) for 3 days followed by 1×PBS (pH=7.4) to remove un-reacted monomer and crosslinker. The purity of the gels is determined by carrying out UV-vis spectroscopy on the supernatant solution. The absence of a peak at 250 nm signifies a purity of the gel. The gels are dried to constant weight.

Drug Loading: 50 mg of gel is soaked in 1.5 ml of 3.5 mg/mL solution of morphine in MILLIQ water for 7 days at 37° C. The supernatant is removed completely and the gels further blotted with filter paper after which they are dried at 40° C. to constant weight.

Figure 19:
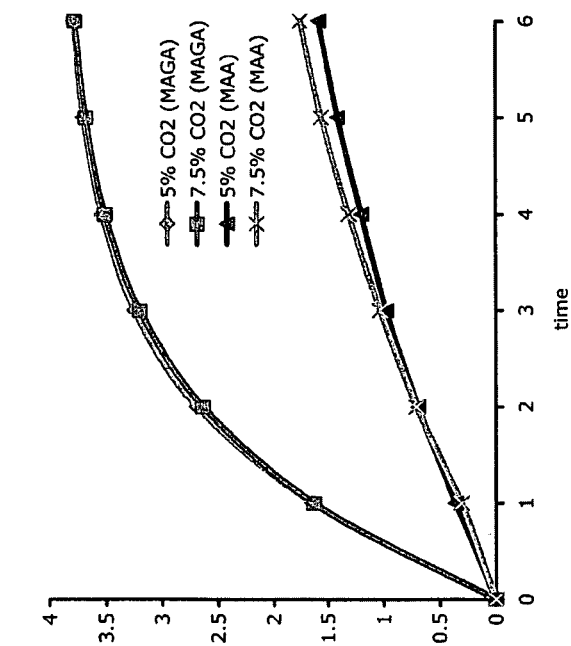
FIG. 19 shows the release of morphine from methacrylic acid and N-methacryloyl glutamic acid gels.
Figure 20A:
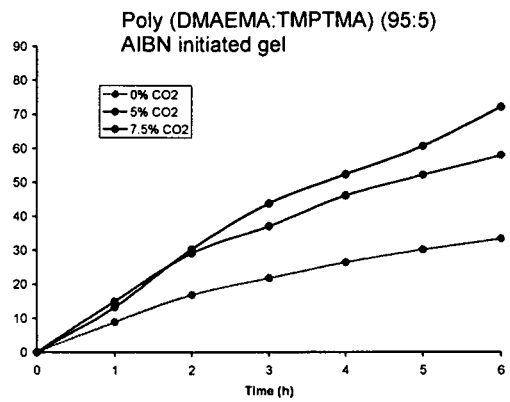
FIG. 20 shows naloxone hydrochloride release from poly (DMAEMA: TMPTMA) a. 95:5, b. 90:10, c. 85:15, d. 80:20.
Figure 20B:
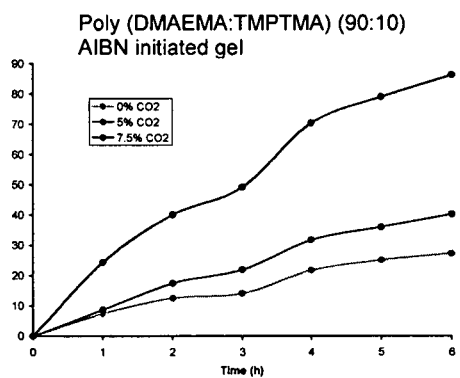
Figure 20C:
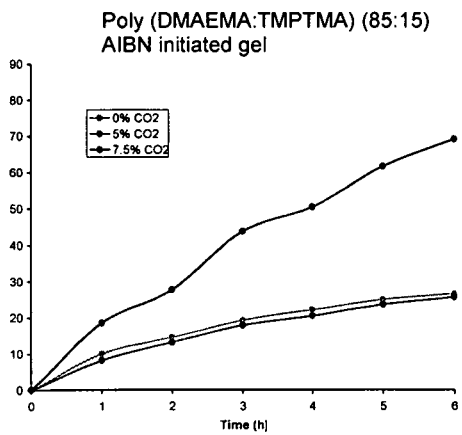
Figure 20D:
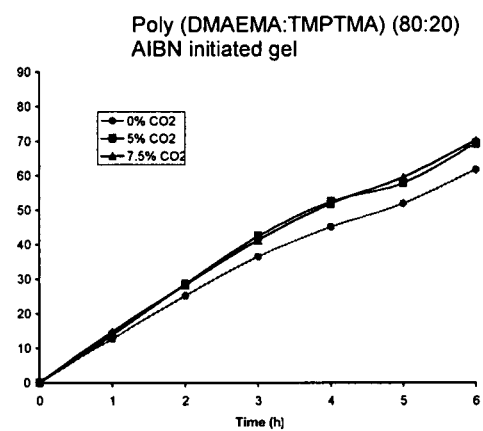

General procedure for drug release study: Dried gel loaded with drug is soaked in 1 mL 1×PBS (pH=7.4) and $CO_2$ (5% and 7.5%) are bubbled through. The buffer solution is completely removed at specific time intervals and the amount of drug released is determined by UV-vis spectroscopy. Results are shown in FIG. 19.

Summary: Both MAA and MAGA gels show a $CO_2$-independent release, but MAGA gels load the drugs better than MAA. MAA provides a more controlled release whilst MAGA provides a burst release.

EXAMPLE 10

DMAEMA-Based Gels for $CO_2$-Responsive Naloxone Release

Scheme 15: Synthesis of DMAEMA-co-TMPTMA gels

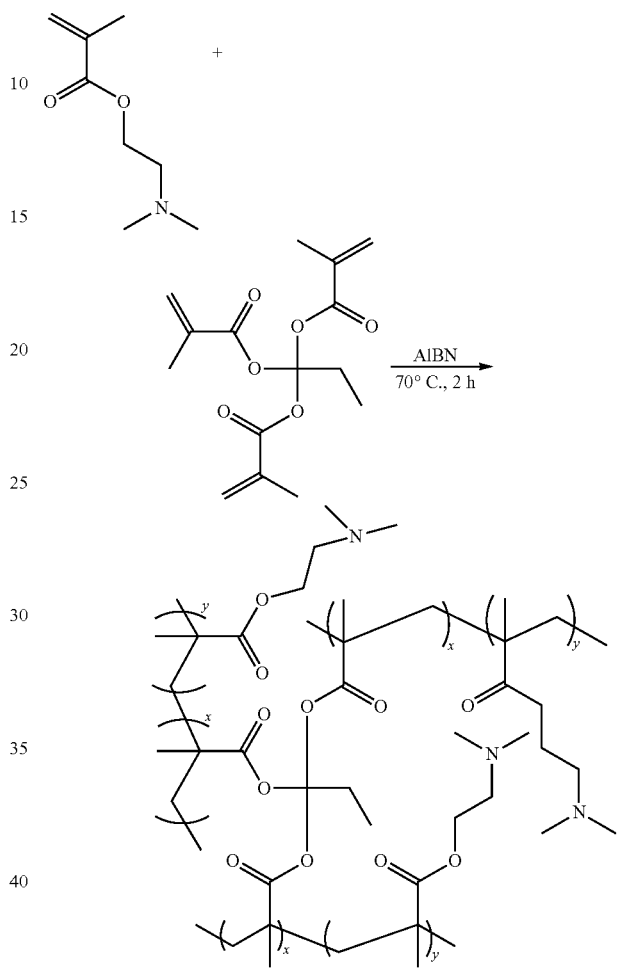

Hydrogel synthesis: DMAEMA and TMPTMA were dissolved in DMF and polymerization was initiated by addition of AIBN and heating the reaction mixture at 70° C. for 2 hours. All the gels were then extensively washed with ethanol and distilled water followed by buffer (PBS) to ensure the absence of UV active impurities. The purified samples were then dried in an oven at 40° C. before naloxone hydrochloride loading. The hydrogels were prepared by varying the co-monomer compositions as DMAEMA:TMPTMA, 95:5, 90:10, 85:15 and 80:20.

TABLE 5

Naloxone loading on (DMAEMA:TMPTMA) hydrogels

| Sample ID | Gel composition DMAEMA:TMPTMA | Naloxone loading mg/g of gel |
|---|---|---|
| SS-VII-128A | 95:5 | 7.23 |
| SS-VII-128C | 90:10 | 5.45 |
| SS-VII-128E | 85:15 | 3.88 |
| SS-VII-128G | 80:20 | 3.30 |

EXAMPLE 11

Naloxone Release from Poly (DEAEMA:PEGMA:TEGDMA) (90:08:02)

Scheme 16: Poly (DEAEMA: PEGMA: TEGDMA) (90:8:2) preparation

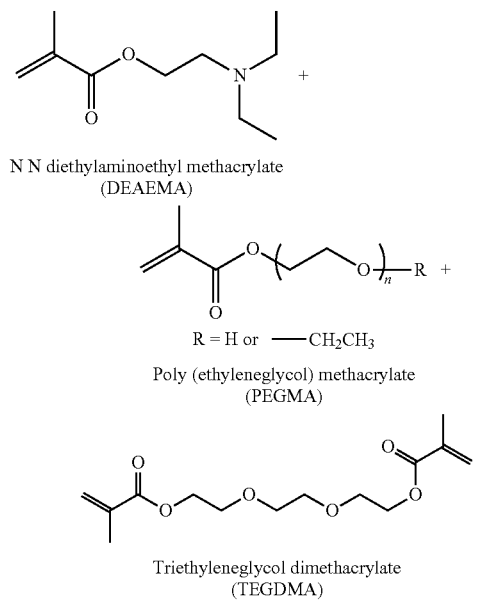

Figure 21:
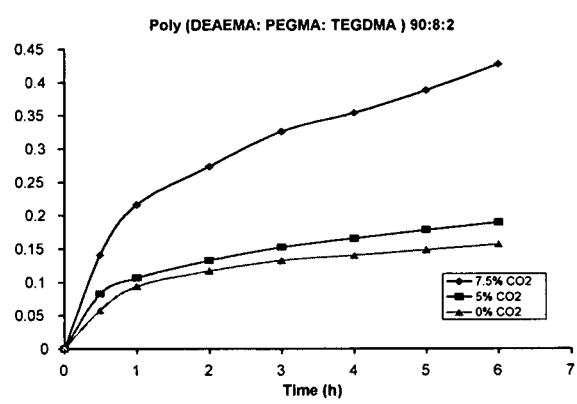
FIG. 21 shows naloxone release from a DEAEMA-co-PEGDA-co-TEGDA gel.
Figure 22A:
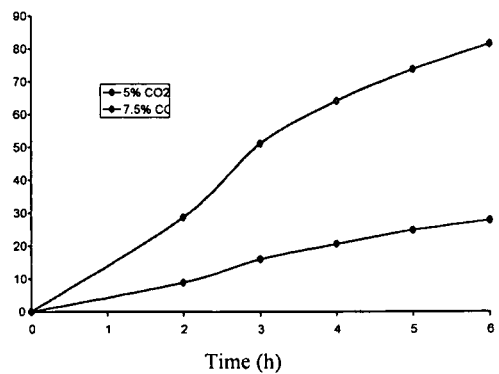
FIG. 22 shows naloxone hydrochloride release from a. control gel, b. in-situ BCA loading, c. Acryloyl modified BCA, d. Methacryloyl modified BCA
Figure 22B:
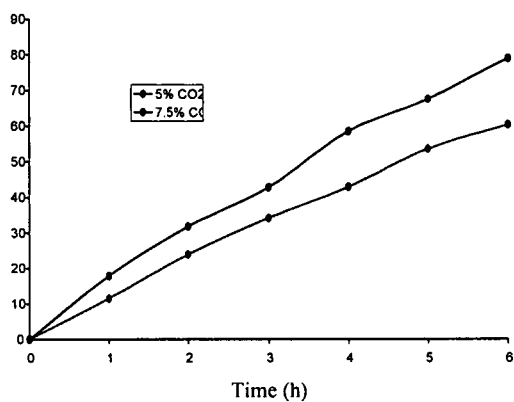
Figure 22C:
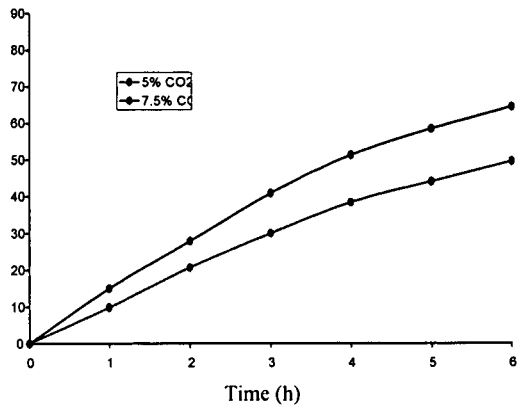
Figure 22D:
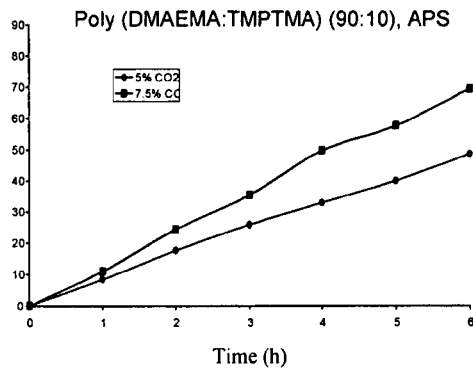

FIG. 21 shows naloxone release from DEAEMA-co-PEGDA-co-TEGDA gel. The $CO_2$ dependence of the drug release shows that this hydrogel has the potential for use as an antidote-releasing delivery vehicle.

EXAMPLE 12

In Situ Incorporation of Bovine Carbonic Anhydrase (BCA)

For in-situ BCA incorporation, 250 μg BCA dissolved in 200 μL PBS buffer pH 7.4 was added during the hydrogel synthesis.

Scheme 17: In-situ incorporation of BCA into the gel

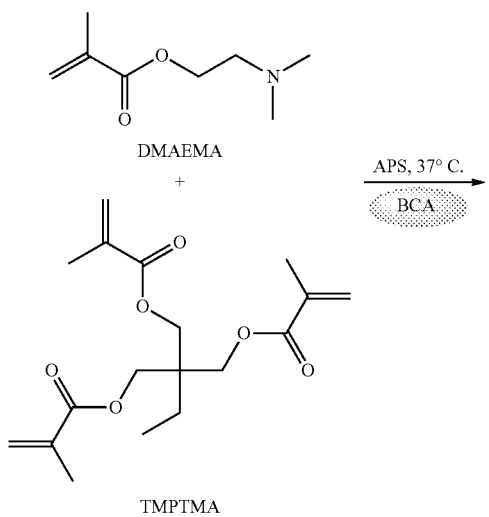

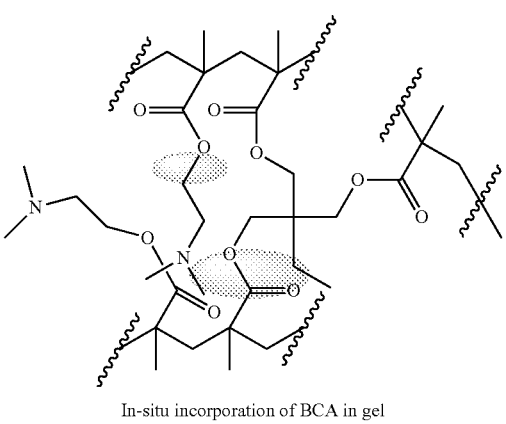

In-situ incorporation of BCA in gel

BCA incorporation can also be done covalently according to the following scheme:

Scheme 17: a. Functionalization of BCA, b. covalent incorporation of of modified BCA into the gel (a)

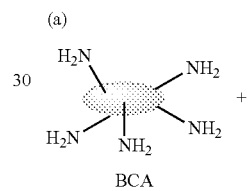

BCA

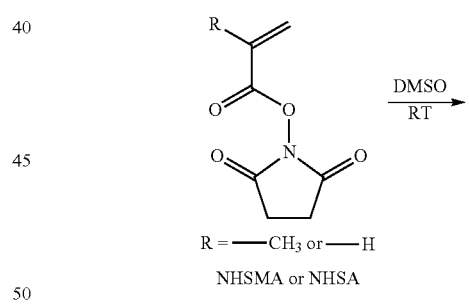

R = —CH₃ or —H
NHSMA or NHSA

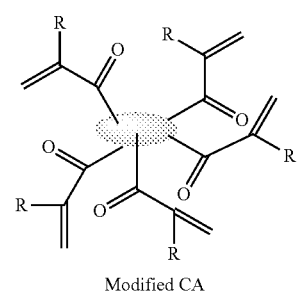

Modified CA

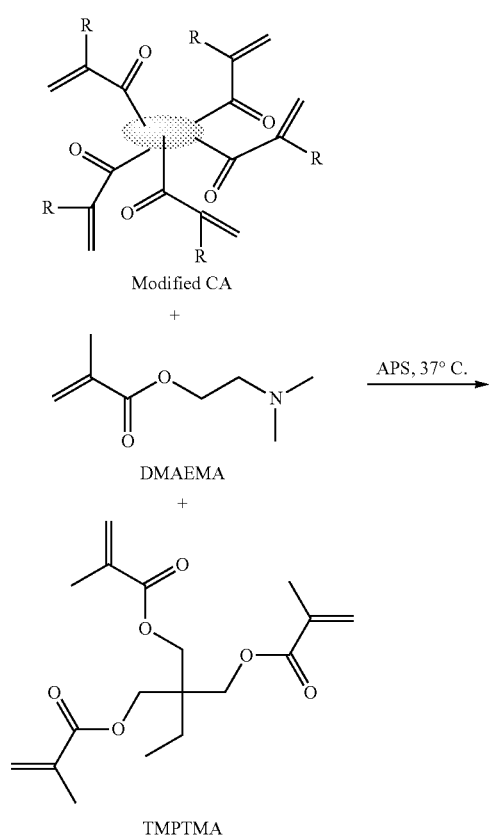

Modified CA + DMAEMA + TMPTMA

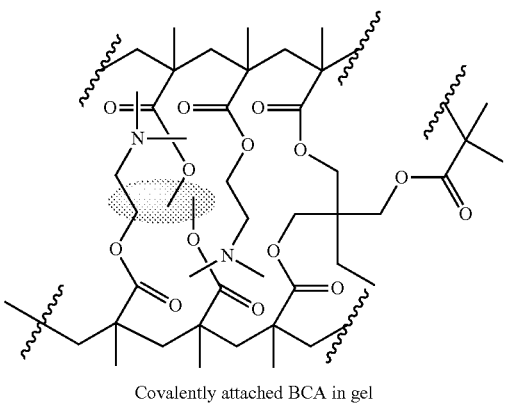 [SMILES: *CC(C)(CC(C)(CC(*)(C)C(=O)OCC(CC)(COC(=O)C(*)(C)C)COC(=O)C(C)(C*)CC(C)(CC(C)(C*)C(=O)OCCN(C)C)C(=O)OC)C(=O)OCCN(C)C)C(=O)OC]

Covalently attached BCA in gel

First the functionalization of BCA was carried out. Typically, 50 mg of BCA was dissolved in 19 ml of pH 9.5, 100 mM boric acid buffer. Next, 25 mg of NHSMA (or NHSA) dissolved in 2 mL DMSO was slowly added, and the reaction was carried out for 2 hours in ice bath. The % modification was measured by performing a literature-reported fluorescamine assay. (FIG. 22)

EXAMPLE 13

MAGA-Based Systems for Controlled ($CO_2$-Independent) Morphine Release

Scheme 18: Synthesis of MAGA-co-SMAG-co-TEGDA gel

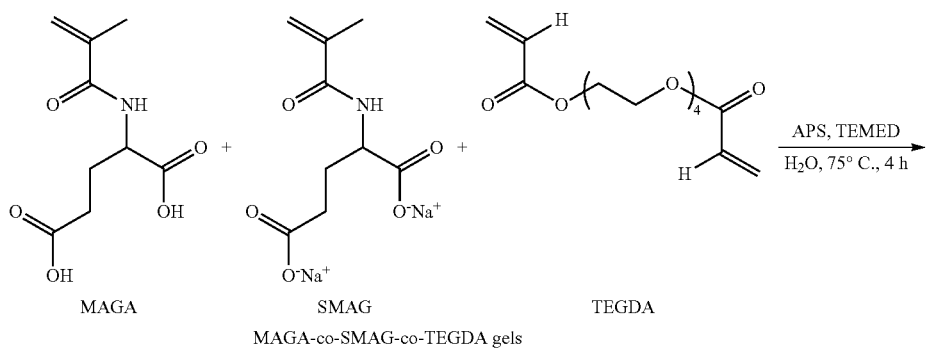

MAGA + SMAG + TEGDA → MAGA-co-SMAG-co-TEGDA gels
(APS, TEMED, $H_2O$, 75° C., 4 h)

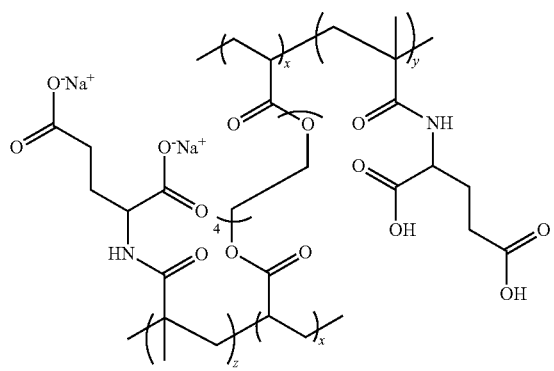

Abbreviations

MAGA: methacryloyl glutamic acid
SMAG: Disodium methacryloyl glutamate
APS: Ammonium persulfate
TEMED: N,N,N',N'-tetramethylethylene diamine Hydrogel Synthesis:

Distilled water was degassed prior to usage. SMAG was prepared by slowly adding MAGA to solution of NaOH (MAGA-to-NaOH 1:2 mol eqv) at 0° C. and stirred at room temperature for 15 minutes. MAGA was added and further stirred for 5 minutes followed by TEGDA and 0.5 ml ethanol to ensure a homogeneous solution. To this mixture was added APS (0.1 mmol, 22.8 mg) and TEMED (0.2 mmol, 22.8 mg) and the mixture was heated at 75° C. for 4 hours. For a 10 mmol mixture of monomers and crosslinker, 3.5 ml of distilled and degassed $H_2O$ was used and 1% mol equivalents of initiator was used. At the end of the reaction, the gel was cooled to ambient temperature and then washed with distilled water for 10 days to remove any unreacted monomers and/or crosslinker. The purity of the gels was confirmed by first carrying out UV-vis spectrophotometry on the supernatant from the washing and further by infra red spectroscopy of the dried gel.

TABLE 6

Composition of MAGA-based gels

| % mol MAGA | % mol SMAG | % mol TEGDA |
|---|---|---|
| 0 | 95 | 5 |
| 45 | 50 | 5 |
| 70 | 25 | 5 |

Drug Loading:

50 mg of gel was soaked in 2 ml of 3.5 mg/ml solution of morphine sulfate pentahydrate for 1 week after which the supernatant was completely removed and the loaded gels were dried at 40° C. to constant weight.

Figure 23:
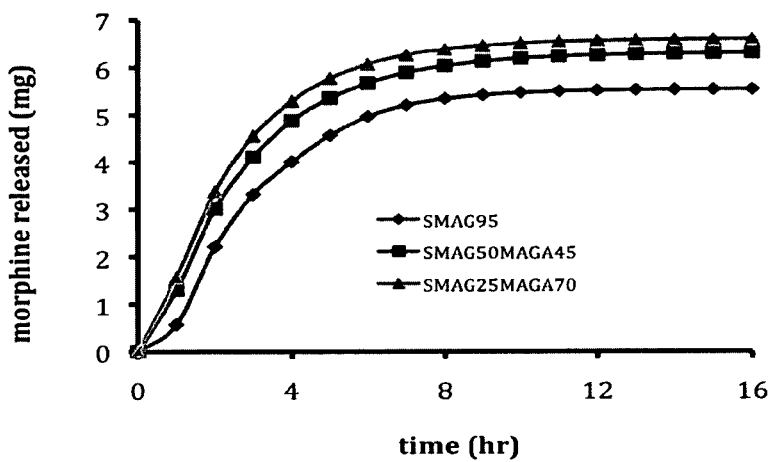
FIG. 23 shows morphine release from MAGA-co-SMAG-co-TEGDA gels.

Release Assay:

The dry loaded gel was soaked in 1 ml 1×PBS (pH 7.4) and the supernatant was removed after every hour. The amount of drug released into the aqueous solution was quantified by UV-vis spectroscopy. (FIG. 23)

MAPhen-Based Hydrogels for Morphine Release

Scheme 19 Synthesis of MAGA-co-SMAPhen-co-TEGDA gel (45:50:5)

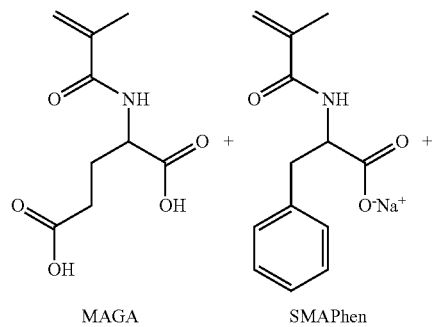

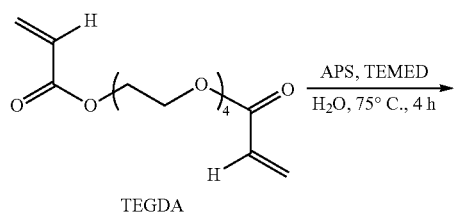

TEGDA

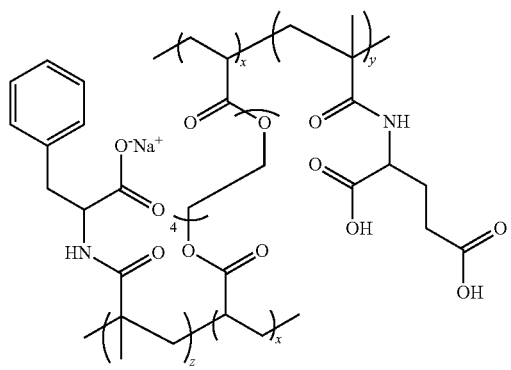

Abbreviation:

SMAPhen—sodium phenylalanate

Figure 24:
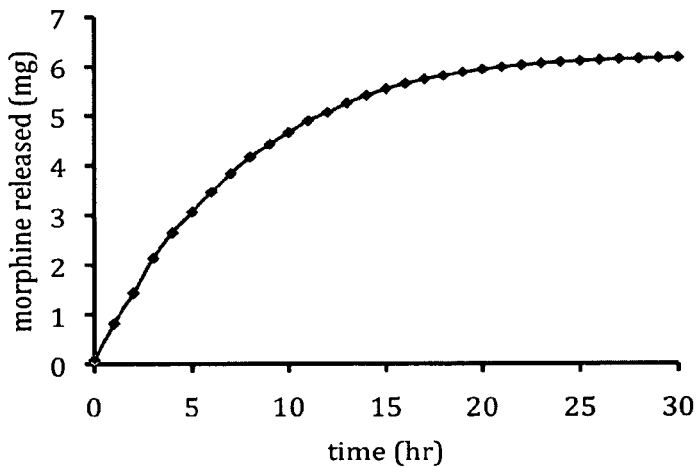
FIG. 24 shows morphine release from MAGA-co-SMAPhen-co-TEGDA gel.

Hydrogel synthesis: Methacryloyl phenylalanine (5.0 mmol, 1.17 g) was dissolved in 4 mL aqueous solution of NaOH (5.0 mmol, 0.2 g) at 0° C. and stirred for 15 minutes after which MAGA (4.5 mmol, 0.97 g) and TEGDA (0.5 mmol, 0.15 g) was added and further stirred for further 10 min. APS and TEMED were added and the mixture was heated for 4 hours. The end of the reaction, the gel was cooled and washed with methanol for 2 months followed by distilled water for 10 days. The purity of the gel was confirmed by first carrying out UV-vis spectroscopy on the supernatant from the washing and further by infra red spectroscopy of the dried gel. (FIG. 24)

EXAMPLE 14

THPMA-Based Gels for $CO_2$ Responsive Naloxone Release

Scheme 20 Synthesis of THPMA-co-HEMA-co-TMPTMA gel

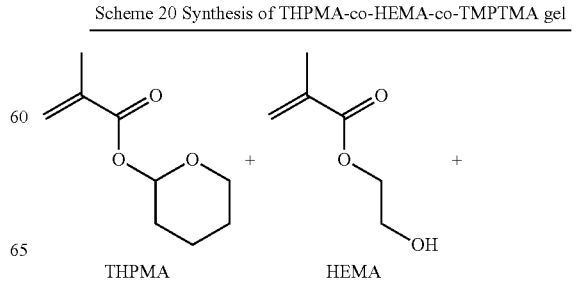

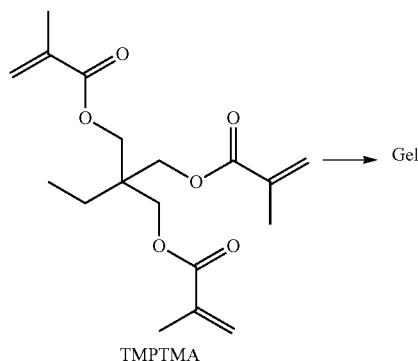

TMPTMA

Abbreviation:

THPMA: Tetrahydropyran methacrylate

HEMA: 2-hydroxyethyl methacrylate

TMPTMA:

Synthesis of THT (47.5%:47.5%:5%) Hydrogel: A stock solution of THPMA (119 μl), HEMA (88 μL) and TMPTMA (24.5 μL) in 34 μL of EtOH was prepared. To this reaction mixture, 10 μL APS (APS stock solution-2 g in 2.5 mL of pH=8.0 PBS buffer) and 10 μL of pH=8.0 PBS buffer was added. To this resultant mixture $N_2$ gas was purged 5 minutes. Finally, 10 μL TEMED was added and the reaction mixture vortexed 1 minute. The polymerization reaction was allowed to proceed for 24 hours at room temperature. The formed hydrogel was washed with ether and pH=8.0 PBS buffer for removing impurities.

FIG. 25 shows the naloxone release from the gel. There is clearly a $CO_2$-dependent release profile in this hydrogel delivery system.

EXAMPLE 15

Ketal-Crosslinked Nanogels

Scheme 21

Synthesis of Nanogels:

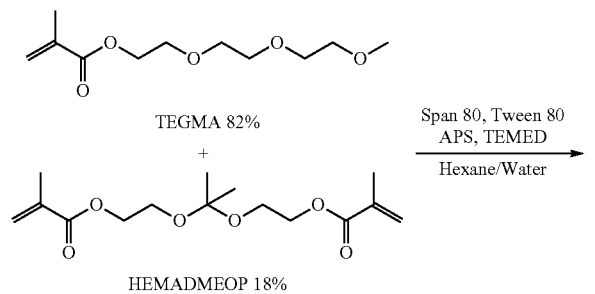

TEGMA 82%
+
HEMADMEOP 18%

Span 80, Tween 80
APS, TEMED
Hexane/Water

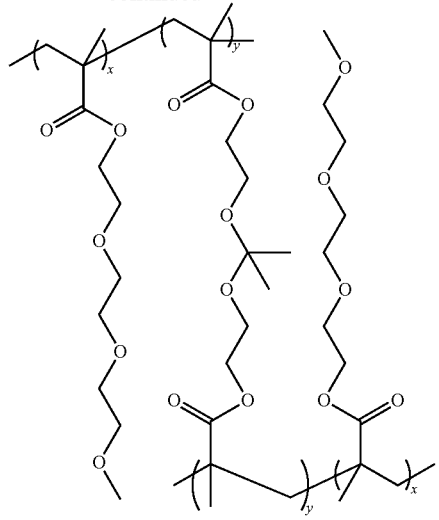

Span 80 (1.2 g), tween 80 (0.4 g) and hexane (50 mL) were dissolved in 250 mL round-bottomed flask. To this solution already prepared mixture (monomer (1.71 g), cross-liner (0.5 g), N,N-dimethylformamide (3 mL) and water (2 mL)) was added immediately. Initiator, ammonium persulfate (0.2 g) was added to start the polymerization and followed by addition of TEMED (0.2 mL) as accelerator then continued the stir for 2 h. Aqueous layer was separated from the mixture and it was three times with hexane (50 mL) to remove the surfactants. It has further purified by dialysis with sodium hydroxide solution (pH 8).

The terms "first," "second," and the like, "primary," "secondary," and the like, as used herein do not denote any order, quantity, or importance, but rather are used to distinguish one element from another. The terms "a" and "an" do not denote a limitation of quantity, but rather denote the presence of at least one of the referenced item.

While the invention has been described with reference to an exemplary embodiment, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A drug delivery vehicle, comprising
a first hydrogel comprising an opioid antagonist, wherein release of the opioid antagonist from the first hydrogel is stimulated by an increase in the concentration of $CO_2$ in environment of the drug delivery vehicle; and
a second hydrogel comprising an opioid, wherein release of the opioid from the second hydrogel is substantially $CO_2$-independent, or is decreased by an increase in the concentration of $CO_2$ in the environment of the drug delivery vehicle,
wherein the second hydrogel comprises 25 to 50 mol % of the aminoalkyl (meth)acrylate of Formula 9

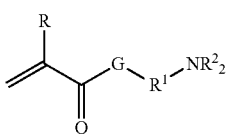

(9)

or an acid salt thereof, wherein G is oxygen or NR' where R' is hydrogen or $C_{1-3}$ alkyl group, R is hydrogen or methyl, $R^1$ is a straight chain or branched $C_{1-4}$ alkylene group, and each $R^2$ is independently hydrogen, $C_{1-4}$ alkyl, or a labile group;

40 to 70 mol % of an acetal (meth)acrylate of Formula 5

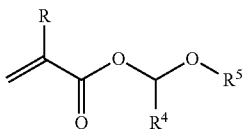

(5)

wherein R is hydrogen or methyl, and each $R^4$ and $R^5$ is independently a straight chain or branched $C_{1-4}$ alkyl group, or $R^4$ and $R^5$ together form a cycloaliphatic ring having a total of 5 to 7 carbon atoms;

and 1 to 5 mol % of a crosslinker of Formula 6

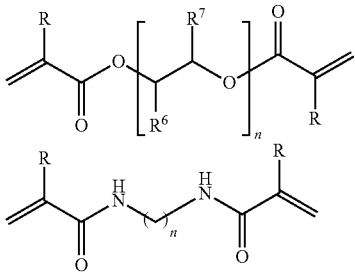

(6)

wherein each R is independently hydrogen or methyl, n is 1 to 4, and $R^6$ and $R^7$ is independently hydrogen or a straight or branched chain $C_{1-3}$ alkyl group, or $R^6$ and $R^7$ together form a cycloaliphatic ring having a total of 5 to 6 carbon atoms or a cycloheteroaliphatic ring having 4 to 6 carbon atoms and an oxygen or sulfur ring atom.

2. The drug delivery vehicle of claim 1, wherein the first hydrogel releases opioid antagonist when the $CO_2$ partial pressure in a gas phase in contact with the environment of the drug delivery vehicle increases from about 36 to about 54 mm Hg.

3. The drug delivery vehicle of claim 1, wherein the first hydrogel comprises a $CO_2$-sensitive group.

4. The drug delivery vehicle of claim 3, wherein the first hydrogel comprises a $CO_2$-sensitive group and is derived from polymerization of a composition comprising 75-99 mol % 2-hydroxyethyl methacrylate, and 1 to 25 mol % of a bis(meth)acrylamide acetal of Formula 1

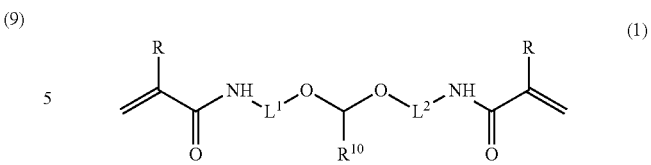

(1)

wherein each $L^1$ and $L^2$ are independently a branched or unbranched $C_{1-4}$ alkylene or $C_{2-4}$ alkenylene, each of which can be unsubstituted or substituted with a hydroxy, carboxy, $C_{1-4}$ alkoxy, phenyl, or phenoxy group, wherein the phenyl or phenoxy group can be unsubstituted or substituted with 1 to 3 hydroxy, carboxy, $C_{1-4}$ alkoxy, phenyl, or phenoxy groups;

wherein each R is independently hydrogen or methyl, $R^{10}$ is a branched or unbranched $C_{1-10}$ alkylene, a $C_{2-10}$ alkenylene, or a phenyl group, each of which can be unsubstituted or substituted with a hydroxy, carboxy, $C_{1-4}$ alkoxy, phenyl, or phenoxy group;

or 1 to 20 mol % 2-hydroxyethyl methacrylate, and 80 to 99 mol % of a divinyl diacetal of Formula 3

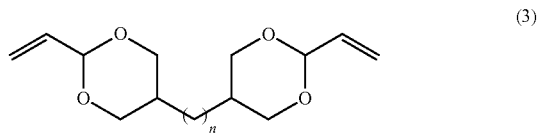

(3)

wherein n comprises 0 to 10 carbon atoms and is optionally substituted with a oxygen, nitrogen, or sulfur.

5. The drug delivery vehicle of claim 4, wherein the bis (meth)acrylamide acetal is of Formula 2

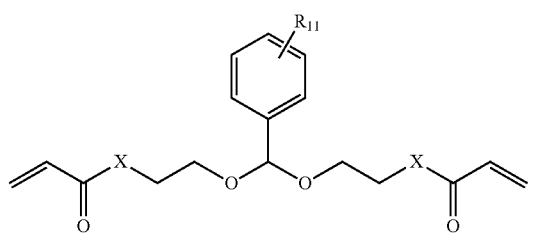

(2)

wherein $R^{11}$ is hydrogen, $C_{1-4}$ alkoxy, or $-O-(C_nH_{2n}O)_m$ $CH_3$, where n=2-3 and m=0-9; and the divinyl acetal is of Formula 4, wherein X is O or NH

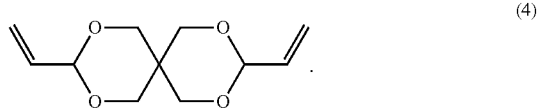

(4)

6. The drug delivery vehicle of claim 3, wherein the first hydrogel comprises a $CO_2$-labile group derived from polymerization of a composition comprising 75 to 99 mol % of an acetal (meth)acrylate of Formula 5

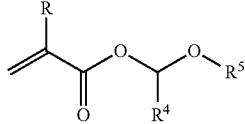
(5)

wherein R is hydrogen or methyl, and each $R^4$ and $R^5$ is independently a straight chain or branched $C_{1-4}$ alkyl group, or $R^4$ and $R^5$ together form a cycloaliphatic ring having a total of 5 to 7 carbon atoms;
and 1 to 25 mol % of a di(meth)acrylate crosslinker of Formula 6

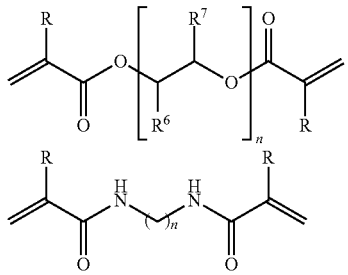
(6)

each R is independently hydrogen or methyl, n is 1 to 4, and $R^6$ and $R^7$ are independently hydrogen or a straight or branched chain $C_{1-3}$ alkyl group, or $R^6$ and $R^7$ together form a cycloaliphatic ring having a total of 5 to 6 carbon atoms or a cycloheteroaliphatic ring having 4 to 6 carbon atoms and an oxygen or sulfur ring atom.

7. The drug delivery vehicle of claim 6, wherein the acetal (meth)acrylate is 2-tetrahydropyranyl methacrylate, and the di(meth)acrylate crosslinker is of Formula 8

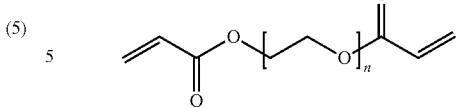
(8)

wherein n is 1 to 4.

8. The drug delivery vehicle of claim 1, wherein the second hydrogel substantially ceases or decreases the opioid release when the $CO_2$ partial pressure increases from about 36 to about 54 mm Hg.

9. The drug delivery vehicle of claim 1, wherein the aminoalkyl (meth)acryate is 2-(dimethylamino)ethyl methacrylate or its hydrochloride salt, the acetal (meth)acrylate is 2-tetrahydropyranyl methacrylate, and the crosslinker is of Formula 8

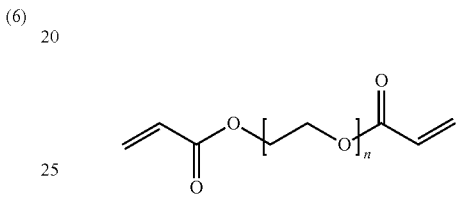
(8)

wherein n=1 to 4.

10. The drug delivery vehicle of claim 1, wherein the second hydrogel releases opioid substantially independent of the $CO_2$ partial pressure.

11. The drug delivery vehicle of claim 1 wherein the first hydrogel, the second hydrogel, or both, is in the form of a nanogel.

12. A method of regulating release of an opioid and/or opioid antagonist from a drug delivery vehicle, comprising
contacting the drug delivery vehicle of claim 1 with an increase in partial pressure of $CO_2$.

* * * * *